US009808517B2

(12) United States Patent
Putnam et al.

(10) Patent No.: US 9,808,517 B2
(45) Date of Patent: Nov. 7, 2017

(54) SUBUNIT VACCINE DELIVERY PLATFORM FOR ROBUST HUMORAL AND CELLULAR IMMUNE RESPONSES

(71) Applicant: CORNELL UNIVERSITY, Ithaca, NY (US)

(72) Inventors: David Putnam, Ithaca, NY (US); Joseph Rosenthal, Ithaca, NY (US); Chung-Jr Huang, Newbury Park, CA (US); Matthew Delisa, Ithaca, NY (US); Susana Mendez, Silver Spring, MD (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 14/390,948

(22) PCT Filed: Mar. 13, 2013

(86) PCT No.: PCT/US2013/031004
§ 371 (c)(1),
(2) Date: Oct. 6, 2014

(87) PCT Pub. No.: WO2013/151706
PCT Pub. Date: Oct. 10, 2013

(65) Prior Publication Data
US 2015/0056246 A1    Feb. 26, 2015

Related U.S. Application Data

(60) Provisional application No. 61/621,226, filed on Apr. 6, 2012.

(51) Int. Cl.
| A61K 51/00 | (2006.01) |
| A61K 39/015 | (2006.01) |
| A61K 39/04 | (2006.01) |
| A61K 39/145 | (2006.01) |
| A61K 39/35 | (2006.01) |
| A61K 39/39 | (2006.01) |
| A61K 38/16 | (2006.01) |
| A61K 39/38 | (2006.01) |
| C12N 15/70 | (2006.01) |
| A61K 39/12 | (2006.01) |
| A61K 39/00 | (2006.01) |

(52) U.S. Cl.
CPC .......... *A61K 39/015* (2013.01); *A61K 38/164* (2013.01); *A61K 39/04* (2013.01); *A61K 39/12* (2013.01); *A61K 39/145* (2013.01); *A61K 39/35* (2013.01); *A61K 39/38* (2013.01); *A61K 39/39* (2013.01); *C12N 15/70* (2013.01); *A61K 2039/52* (2013.01); *A61K 2039/523* (2013.01); *A61K 2039/6068* (2013.01); *C12N 2760/16134* (2013.01)

(58) Field of Classification Search
CPC ........ A61K 39/00; A61K 38/48; A61K 48/00; A61K 39/08; A61K 39/015; C12N 1/00

USPC ................................. 424/93.2, 780
See application file for complete search history.

(56) References Cited

U.S. PATENT DOCUMENTS

| 4,009,258 A * | 2/1977 | Kilbourne ............ A61K 39/145 424/206.1 |
| 7,056,700 B2 | 6/2006 | Galen |
| 7,329,807 B2 | 2/2008 | Vadricco et al. |
| 7,732,580 B2 | 6/2010 | Chang |
| 7,763,420 B2 * | 7/2010 | Stritzker ................ A61K 33/24 424/234.1 |
| 7,820,184 B2 * | 10/2010 | Stritzker ................ A61K 33/24 424/234.1 |
| 8,303,964 B2 * | 11/2012 | Woodard ................... 424/249.1 |
| 8,349,586 B1 * | 1/2013 | Hamer ................. A61K 35/741 424/93.21 |
| 8,524,220 B1 * | 9/2013 | Bermudes ............... C07K 14/81 424/780 |
| 8,771,669 B1 * | 7/2014 | Bermudes ............... A61K 35/74 424/93.2 |
| 9,051,565 B2 * | 6/2015 | Delisa ................. C12N 15/1037 |
| 9,125,864 B2 * | 9/2015 | Grifantini ............ A61K 39/118 |
| 9,140,698 B2 * | 9/2015 | Orth .................. G01N 33/56911 |
| 2002/0146430 A1 | 10/2002 | Galen |
| 2005/0180962 A1 * | 8/2005 | Raz ........................ A23L 1/3014 424/93.45 |

(Continued)

FOREIGN PATENT DOCUMENTS

| CN | 101827943 A | 9/2010 |
| HK | 1005465 A | 11/1994 |

(Continued)

OTHER PUBLICATIONS

Proteomics, 2014, vol. 14, pp. 222-229, Aguilera, L et al, Proteomic analysis of outer membrane vesicles from the probiotic strain *Escherichia coli* Nissle 1917.*

Bermudez-Humaran et al., "Lactococci and Lactobacilli as Mucosal Delivery Vectors for Therapeutic Proteins and DNA Vaccines," Microb Cell Fact. 10(Suppl 1)(S4:1-10 (2011).

Arribas et al., "A Probiotic Strain of *Escherichia coli*, Nissle 1917, Given Orally Exerts Local and Systemic Anti-inflammatory Effects in Lipopolysaccharide-induced Sepsis in Mice," Br J Pharmacol. 157(6):1024-1033 (2009).

(Continued)

*Primary Examiner* — Albert Navarro
(74) *Attorney, Agent, or Firm* — LeClairRyan, a Professional Corporation

(57) ABSTRACT

The present invention relates to a probiotic cell transformed with a construct suitable to overexpress and display on the surface of the probiotic cell a fusion protein comprising at least a portion of a transport protein coupled to at least a portion of one or more antigenic proteins or peptides. Probiotic-derived vesicles displaying this fusion protein as well as methods of inducing an immune response using the probiotic cells or vesicles are also disclosed.

44 Claims, 19 Drawing Sheets

(56) References Cited

U.S. PATENT DOCUMENTS

| | | | | |
|---|---|---|---|---|
| 2006/0094117 | A1* | 5/2006 | Hacker | A61K 35/74 435/488 |
| 2006/0216307 | A1* | 9/2006 | Berthet | A61K 39/095 424/190.1 |
| 2007/0082164 | A1* | 4/2007 | Sellers | A47J 36/34 428/43 |
| 2007/0207526 | A1* | 9/2007 | Coit | A61K 39/12 435/91.1 |
| 2007/0248573 | A1* | 10/2007 | Sturino | A61K 35/76 424/93.6 |
| 2008/0193373 | A1* | 8/2008 | Stritzker | A61K 33/24 424/1.17 |
| 2009/0035326 | A1* | 2/2009 | Contorni | A61K 39/02 424/196.11 |
| 2009/0081202 | A1* | 3/2009 | Fischer | A61K 39/085 424/130.1 |
| 2009/0180987 | A1* | 7/2009 | Stritzker | A61K 33/24 424/93.2 |
| 2009/0238804 | A1* | 9/2009 | Oswald | C12R 1/19 424/93.21 |
| 2009/0324638 | A1* | 12/2009 | Dattwyler | A61K 39/0225 424/200.1 |
| 2010/0233195 | A1* | 9/2010 | Delisa | C12N 15/1037 424/184.1 |
| 2011/0008392 | A1* | 1/2011 | Buck | A61K 39/002 424/269.1 |
| 2011/0166323 | A1* | 7/2011 | Masignani | C07K 14/22 530/350 |
| 2011/0251156 | A1* | 10/2011 | Shen | A61K 31/715 514/54 |
| 2013/0115238 | A1* | 5/2013 | Pizza | A61K 39/095 424/190.1 |
| 2013/0195907 | A1* | 8/2013 | Grifantini | A61K 39/118 424/190.1 |
| 2015/0150959 | A1* | 6/2015 | Watnick | A61K 39/02 424/179.1 |
| 2016/0169921 | A1* | 6/2016 | Orth | G01N 33/56911 435/7.2 |

FOREIGN PATENT DOCUMENTS

| | | | | |
|---|---|---|---|---|
| WO | 93/17117 | A1 | 9/1993 | |
| WO | 2005/064021 | * | 7/2005 | C12R 1/36 |
| WO | 2008/073148 | * | 5/2008 | G01N 33/50 |
| WO | 2008/115061 | * | 9/2008 | A61K 47/48 |
| WO | 2010/010983 | * | 1/2010 | C12N 15/00 |
| WO | 2011161551 | * | 12/2011 | C12N 1/00 |
| WO | 2012019058 | A1 | 2/2012 | |
| WO | 2012/041899 | * | 4/2012 | C12N 15/62 |

OTHER PUBLICATIONS

Li et al., "Strain-dependent Induction of Allergic Sensitization Caused by Peanut Allergen DNA Immunization in Mice," J Immunol. 162(5):3045-3052 (1999).

Forbes, "Engineering the Perfect (bacterial) Cancer Therapy," Nat Rev Cancer 10(11:785-794 (2010).

Stritzker et al., "Tumor-specific Colonization, Tissue Distribution, and Gene Induction by Probiotic *Escherichia coli* Nissle 1917 in Live Mice,".

International Search Report and Written Opinion for corresponding PCT/US13/31004 (mailed Jul. 1, 2013).

Chen et al., "Engineering Outer Membrane Vesicles for Gene Delivery," School of Chemical and Biomolecular Engineering, Cornell University, Department of Biomedical Engineering, Ithaca, NY at: http://aiche.confex.com/aiche/2006/techprogram/P70675. HTM, pp. 1-2 (Printed Jul. 17, 2008).

Dhandayuthapani et al., "Green Fluorescent Protein as a Marker for Gene Expression and Cell Biology of Mycobacterial Interactions with Macrophages," Molecular Microbiology 17(5):901-12 (1995).

Galen et al., "Adaptation of the Endogenous *Salmonella enterica* Serover Typhi clyA-Encoded Hemolysin for Antigen Export Enhances the Immunogenicity of Anthrax Protective Antigen Domain 4 Expressed by the Attenuated Live-Vector Vaccine Strain CVD 908-htrA," Infection and Immunity 72(12):7096-106 (2004).

Georgiou et al., "Display of Heterologous Proteins on the Surface of Microorganisms: From the Screening of Combinatorial Libraries to Live Recombinant Vaccines," Nature Biotechnology 15:29-34 (1997).

International Search Report and Written Opinion for International Patent Application No. PCT/US08/64376 (Oct. 27, 2008).

Kim et al., "Strategies for Expanding the Repertoire of Proteins that can be Displayed on the Outer Surface of *E. coli*," School of Chemical and Biomolecular Engineering, Cornell University, Ithaca, NY at: http://aiche.confex.com/aiche/2005/techprogram/P22253.HTM, p. 1 (Printed Oct. 3, 2008).

Wai et al., "Vesicle-Mediated Export and Assembly of Pore-Forming Oligomers of the Enterobacterial ClyA Cytotoxin," Cell 115:25-35 (2003).

Del Castillo et al., "Secretion of the *Escherichia coli* K-12 SheA Hemolysin is Independent of its Cytolytic Activity," FEMS Microbiol. Lett. 204(2):281-285 (2001).

Kim et al., "Engineered Bacterial Outer Membrane Vesicles with Enhanced Functionality," J. Mol. Biol. 380(1):51-66 (2008).

Bernadac et al., "*Escherichia coli* tol-pal Mutants Form Outer Membrane Vesicles," J. Bacteriol. 180:4872-4878 (1998).

Extended European Search Report for European Patent Application No. 13772865.5, (Jun. 10, 2016).

English Translation and First Office Action for Corresponding China Application No. 201380029408.5 (Dec. 26, 2016).

\* cited by examiner

SUBUNIT VACCINE DELIVERY PLATFORM FOR ROBUST HUMORAL AND CELLULAR IMMUNE RESPONSES

This application is a national stage application under 35 U.S.C. §371 from PCT Application No. PCT/US2013/031004, filed Mar. 13, 2013, which claims the benefit of U.S. Provisional Patent Application Ser. No. 61/621,226, filed Apr. 6, 2012, which are hereby incorporated by reference in their entirety.

This invention was made with government support under National Institutes of Health Grant No. EB005669-02. The government has certain rights in this invention.

FIELD OF THE INVENTION

The present invention relates to a subunit vaccine delivery platform for robust humoral and cellular immune responses.

BACKGROUND OF THE INVENTION

Recent advances in vaccine delivery system engineering have succeeded in refining the antigen-immune cell interface to substantially improve the adaptive immune response to recombinant subunit vaccine antigens (Azad et al., "Vaccine Delivery—Current Trends and Future," *Curr. Drug Deliv.* 3:137-146 (2006); Schijns and Degen, "Vaccine Immunopotentiators of the Future," *Clin. Pharmacol. Ther.* 82:750-755 (2007); Huang et al., "Recombinant Immunotherapeutics: Current State and Perspectives Regarding the Feasibility and Market," *Appl. Microbiol. Biotechnol.* 87:401-410 (2010); Swartz et al., "Engineering Approaches to Immunotherapy," *Sci. Transl. Med.* 4 (2012)). Increasingly, this success has come from innovations in the application of synthetic or biologically-derived nanoparticle antigen carriers (Swartz et al., "Engineering Approaches to Immunotherapy," *Sci. Transl. Med.* 4 (2012); Singh et al., "Nanoparticles and Microparticles as Vaccine-Delivery Systems," *Expert Rev. Vaccines* 6:797-808 (2007); Metcalfe and Fahmy, "Targeted Nanotherapy for Induction of Therapeutic Immune Responses," *Trends Mol. Med.* 18:72-80 (2012)). Nanoparticulate carriers have succeeded in capturing more holistic interactions with pathogens that extend beyond simple antigen identification (Bryan, "Developing an HPV Vaccine to Prevent Cervical Cancer and Genital Warts," *Vaccine* 25:3001-3006 (2007)), and allow more efficient and targeted dissemination of antigen to key immune cell populations (Sanders et al., "ISCOM-Based Vaccines: the Second Decade," *Immunol Cell Biol* 83:119-129 (2005)). By transitioning the focus of vaccine design to biomolecular and materials engineering, important barriers of adaptive immunity engagement and effective memory response enhancement have been effectively challenged. With this success, however, it has become clear that there remains a marked inability of current subunit vaccine technology to generate protective pathogen-specific $T_H1$-biased cellular immunity (Bevan, "Understand Memory, Design Better Vaccines," *Nat. Immunol.* 12:463-465 (2011)) while addressing pathogenic source-related constraints (Huang et al., "Recombinant Immunotherapeutics: Current State and Perspectives Regarding the Feasibility and Market," *Appl. Microbiol. Biotechnol.* 87:401-410 (2010); Yoo et al., "Bio-Inspired, Bioengineered and Biomimetic Drug Delivery Carriers," *Nat. Rev. Drug Discov.* 10:521-535 (2011)) such as the compatibility challenge of recombinant antigen integration and minimizing the risk of disease transmission. Similarly, challenges pertaining to global health applications of novel, often prohibitively expensive vaccine technology also remain markedly unsolved.

The present invention in directed to overcoming these and other deficiencies in the art.

SUMMARY OF THE INVENTION

A first aspect of the present invention relates to a probiotic cell transformed with a construct suitable to overexpress and display on the surface of the probiotic cell a fusion protein comprising at least a portion of a transport protein coupled to at least a portion of one or more antigenic proteins or peptides.

The present invention is also directed to a probiotic-derived vesicle displaying a fusion protein, where said fusion protein comprises at least a portion of a transport protein coupled to at least a portion of one or more antigenic proteins or peptides.

Another aspect of the present invention relates to a probiotic cell transformed with a construct suitable to overexpress and display on the surface of the probiotic cell a fusion protein comprising at least a portion of a transport protein coupled to at least a portion of one or more antigenic food allergy proteins or peptides.

A further aspect of the present invention relates to a probiotic-derived vesicle displaying a fusion protein, where said fusion protein comprises at least a portion of a transport protein coupled to at least a portion of one or more antigenic food allergy proteins or peptides.

The present invention is also directed to a probiotic cell transformed with a construct suitable to overexpress and display on the surface of the probiotic cell a fusion protein comprising at least a portion of a transport protein coupled to at least a portion of one or more antigenic viral proteins or peptides.

Yet another aspect of the present invention relates to a probiotic-derived vesicle displaying a fusion protein, where said fusion protein comprises at least a portion of a transport protein coupled to at least a portion of one or more antigenic viral proteins or peptides.

A further aspect of the present invention relates to a probiotic cell transformed with a construct suitable to overexpress and display on the surface of the probiotic cell a fusion protein comprising at least a portion of a transport protein coupled to at least a portion of one or more antigenic intracellular bacterial proteins or peptides.

A final aspect of the present invention relates to a probiotic-derived vesicle displaying a fusion protein, where said fusion protein comprises at least a portion of a transport protein coupled to at least a portion of one or more antigenic intracellular bacterial proteins or peptides.

To address the limitations of subunit vaccines and the broad unmet clinical need they represent, the engineering of biologically-derived pathogen-like particles derived from the outer membrane of gram-negative bacteria was considered. Outer membrane vesicle (OMV)-based vaccines produced directly from pathogens, in particular *Neisseria meningitides*, have been successful at preventing disease (Granoff, "Review of Meningococcal Group B Vaccines," *Clin. Infect. Dis.* 50:S54-S65 (2010), which is hereby incorporated by reference in its entirety). Additionally, recent literature indicates that OMVs have inherent roles in natural bacterial virulence and possess general adjuvant capabilities that may be broadly applicable. Specifically, there is compelling evidence that OMVs—although non-infectious— retain much of the capacity of live bacteria to holistically engage both the innate and adaptive immune system, through a host of surface displayed and soluble-factor intracellular pathogen-associated molecular patterns (PAMPs) (Ellis and Kuehn, "Virulence and Immunomodulatory Roles of Bacterial Outer Membrane Vesicles," *Microbiol. Mol. Biol. Rev.* 74:81-94 (2010); Kulp and Kuehn, "Biological Functions and Biogenesis of Secreted Bacterial Outer Membrane Vesicles," *Annu. Rev. Microbiol.* 64:163-184 (2010); Kuehn and Kesty, "Bacterial Outer Membrane Vesicles and the Host-Pathogen Interaction," *Genes Dev.* 19:2645-2655 (2005), each of which is hereby incorporated by reference in its entirety). These characteristics have inspired recent work with multi-strain meningococcal OMV vaccines (Zollinger et al., "Design and Evaluation in Mice of a Broadly Protective Meningococcal Group B Native Outer membrane Vesicle Vaccine," *Vaccine* 28:5057-5067 (2010), which is hereby incorporated by reference in its entirety) and even cross-pathogen antigen presentation (Muralinath et al., "Immunization with *Salmonella Enterica* Serovar *Typhimurium*-Derived Outer Membrane Vesicles Delivering the Pneumococcal Protein PspA Confers Protection Against Challenge with *Streptococcus Pneumonia*," *Infect. Immun.* 79:887-894 (2011), which is hereby incorporated by reference in its entirety), and indicates that such natural adjuvancy has the capacity to potentiate organism-specific immune responses not yet achievable with standard subunit vaccines. Combined with their cost-effective production in scalable bacterial culture, OMVs are promising vaccine formulations (Granoff, "Review of Meningococcal Group B Vaccines," *Clin. Infect. Dis.* 50:S54-S65 (2010), which is hereby incorporated by reference in its entirety). However, to date, engineered OMV vaccines with applications beyond the original source-strain have been limited (Ellis and Kuehn, "Virulence and Immunomodulatory Roles of Bacterial Outer Membrane Vesicles," *Microbiol. Mol. Biol. Rev.* 74:81-94 (2010); Muralinath et al., "Immunization with *Salmonella Enterica* Serovar *Typhimurium*-Derived Outer Membrane Vesicles Delivering the Pneumococcal Protein PspA Confers Protection Against Challenge with *Streptococcus Pneumonia*," *Infect. Immun.* 79:887-894 (2011), each of which is hereby incorporated by reference in its entirety), with the focus almost entirely on the "native OMV" approach that only explores the applicability of a pathogen's own OMVs as a vaccine exclusively against itself.

Noting that the untapped potential of OMVs aligned well with key limitations of subunit vaccines, whether a generally applicable and highly immunostimulatory, self-adjuvanting recombinant vaccine delivery platform could be created from OMVs derived from Gram-negative probiotic bacteria was investigated. During colonization of the human digestive tract, certain probiotic bacteria suppress local immunity by modulating resident gut-associated lymphoid tissue cytokine activity (Trebichaysky et al., "Modulation of Natural Immunity in the Gut by *Escherichia Coli* Strain Nissle 1917," *Nutr. Rev.* 68:459-464 (2010), which is hereby incorporated by reference in its entirety). Noting that one of the most consistent deficiencies in modern vaccines is the ability to stimulate cellular immunity, bacteria were sought whose immunomodulatory capacity was characterized by potent interactions with cell types crucial for $T_H1$-biased immunity. Specifically, the focus was on the probiotic *E. coli* strain Nissle 1917 (EcN), which achieves this phenomenon in part through specifically targeting T-leukocytes for disruption via strain-specific PAMP-dependent mechanisms (Sturm et al., "*Escherichia Coli* Nissle 1917 Distinctively Modulates T-Cell Cycling and Expansion Via Toll-Like Receptor 2 Signaling," *Infect. Immunol.* 73:1452-1465 (2005); Guzy et al., "The Probiotic *Escherichia Coli* Strain Nissle 1917 Induces Gammadelta T Cell Apoptosis Via Caspase- and FasL-Dependent Pathways," *Int. Immun.* 20:829-840 (2008), each of which is hereby incorporated by reference in its entirety). Such potent suppressive capacity does not make EcN, or any probiotic bacteria, an obvious candidate for vaccine applications. However, in marked contrast to the highly immunosuppressive bacteria themselves, OMVs derived from such Gram-negative probiotic bacteria lack the predominantly secretory immunosuppressive capability while retaining surface-displayed immunostimulatory PAMPs and, in EcN's case, the rare capacity to actively bind to and stimulate T-cell Toll-like receptors (TLRs) (Sturm et al., "*Escherichia Coli* Nissle 1917 Distinctively Modulates T-Cell Cycling and Expansion Via Toll-Like Receptor 2 Signaling," *Infect. Immunol.* 73:1452-1465 (2005), which is hereby incorporated by reference in its entirety). Therefore, it was hypothesized that OMVs comprised of the uniquely immunostimulatory EcN outer membrane could effectively leverage a probiotic strain's distinctive ability to engage and activate key innate and adaptive immune cells (Mohamadzadeh et al., "Dendritic Cell Targeting of *Bacillus Anthracis* Protective Antigen Expressed by *Lactobacillus Acidophilus* Protects Mice From Lethal Challenge," *Proc. Nat. Acad. Sci. USA* 106:4331-4336 (2009), which is hereby incorporated by reference in its entirety), while simultaneously enhancing the natural adjuvanting mechanisms through which OMVs interact with immune cells and effectively mimic intracellular pathogens. If this hypothesis were validated, the resulting pathogen-like particles would have the potential to robustly couple carrier-presented recombinant exogenous antigens with both humoral and cellular immune responses.

The present invention shows that the immunization of mice with OMVs engineered to surface display exogenous model antigens induces robust antigen-specific humoral and cellular immunity. More importantly, both the development of humoral immunity through antibody class selection as well as the preferential development of specific CD4/CD8-positive T-cell cytokine expression phenotypes strongly indicates the induction of antigen-specific $T_H1$-biased immunity. In vitro and in vivo mechanistic analyses of the immune response to the OMVs reveals an immune reaction specific to the strain that makes use of their unique combination of PAMP-TLR interactions, mediated through stimulation of both innate and adaptive immune cells. These results indicate an effectively engineered isolation of probiotic bacterial immunoactivity that has a previously unappreciated capacity as a scalable (Granoff, "Review of Meningococcal Group B Vaccines," *Clin. Infect. Dis.* 50:S54-S65 (2010), which is hereby incorporated by reference in its entirety) and broadly applicable vaccine delivery carrier for challenging pathogen targets requiring strong, targeted $T_H1$-mediated immunity.

BRIEF DESCRIPTION OF THE DRAWINGS

FIG. 1A shows OMV overproduction was achieved in EcN via a marked deletion of nlpI as illustrated here on a genetic map of the *E. coli* genome, 71.0-71.1 min. FIG. 1B shows FE-SEM micrographs (left panel) and demonstrates predominantly uniform size and shape of EcN OMVs, while TEM micrographs (right panel) highlight characteristic bilipid membrane. Scale bars=200 nm. FIG. 1C shows a fluorescent micrograph of ultracentrifugation-purified OMVs from EcN cultures transformed with ClyA-GFP-containing plasmid. FIG. 1D shows Western blot with anti-GFP antibodies of OMV suspensions from EcN and EcJ cultures transformed with ClyA-GFP-containing plasmid. FIG. 1E shows membrane-bound LPS in fluorescence-standardized 100 µL doses of ClyA-GFP EcN and EcJ OMVs determined via KDO colorimetric assay (mean+s.d.). Protein levels determined quantitatively to biological relevance by iTRAQ protein mass spectrometry. Omp=outer membrane protein, OMLP=outer membrane lipoprotein.

FIG. 2A-2H shows terminal data points from BALB/c mice vaccinated and boosted once with antigen-normalized (or protein normalized, as appropriate) doses of (FIG. 2A-2C, FIG. 2E-2H) purified GFP, ClyA, ClyA+GFP, ClyA-GFP(+) and (−) EcJ OMVs, ClyA-GFP(+) and (−) EcN OMVs, ClyA-GFP+Alum, and PBS (n=5) or (FIG. 2D) PBS, purified H1N1 influenza hemagglutinin (HA), H1N1 HA+Alum, and ClyA-H1N1 HA (+) EcN OMVs (n=5). (FIG. 2A-2B) Class-specific anti-GFP antibody serum titers. FIG. 2C shows the ratio of serum titers of IgG1 to IgG2. FIG. 2D shows hemagglutinin inhibition assay serum titers. FIG. 2E shows the proliferation index of GFP-restimulated spleen-derived T-cells harvested from end-point subjects, measured via CFSE stain. FIG. 2F-2H show cytokine secretion levels from cultured, GFP-restimulated spleen-derived T-cells harvested from end-point subjects. FIG. 2A-2C, FIG. 2E-2H GFP* data are representative of ClyA, ClyA+GFP, ClyA-GFP (−) ECJ and EcN OMVs, and PBS control subjects. In FIG. 2A-2H Alum=Alhydrogel®. P<0.001, *P<0.05 determined by Tukey's HSD post-hoc test. All values are given as mean+s.d.

FIG. 3A-3D shows histological sections from BALB/c mice ears injected subdermally with equivalent doses of: (FIG. 3A) PBS; (FIG. 3B) EcJ OMVs; (FIG. 3C) EcN OMVs; (FIG. 3D) LpxM EcN OMVs. Mice were sacrificed after 30 h. Increased tissue remodeling, vasculature swelling, and leukocyte recruitment (as indicated by arrows) can be seen in FIG. 3B relative to FIG. 3A, are significantly enhanced in FIG. 3C, and are attenuated but not removed in FIG. 3D. FIG. 3E shows the percentage of primary mouse bone marrow-derived macrophages (BMMs) positive for GFP after 12 h incubation with ClyA-GFP(+) OMVs. FIG. 3F shows the percentage of BMMs expressing cytokines IL-12, IL-4, and IL-10 after 12 h incubation with OMVs. FIG. 3G shows the proliferation of primary mouse spleen-derived T-cells following co-culture with mouse bone-marrow derived dendritic cells pre-incubated with equivalent amounts of EcJ and EcN OMVs. RPMI=negative control, αCD3/αCD26=positive control. FIG. 3H shows the proliferation of primary mouse bone marrow-derived B-cells following incubation with OMVs, with or without additional T-cell helper factors. RPMI* data are representative of additional controls αIgM, αCD40, and IL-4. LPS** data are representative of additional controls αIgM/IL-4 and αCD40/IL-4. In FIG. 3E-3H, *P<0.001, P<0.05, *P<0.005 determined by Tukey's HSD post-hoc test. All values are given as mean+s.d.

FIG. 4A shows the natural immunosuppressive function of Nissle 1917 E. coli (EcN), focusing on direct effector action on αβ T-lymphocytes. Membranous, strain-specifically glycosylated bacterial lipopolysaccharide (LPS) and bacterial lipoproteins (BLPs), as well as secreted BLPs and other assorted secreted factors (ASFs), target the T-cells and transduce modulatory signals through Toll-like receptors (TLRs) TLR-2 and TLR-4 (Granoff, "Review of Meningococcal Group B Vaccines," Clin. Infect. Dis. 50:S54-S65 (2010); Trebichaysky et al., "Modulation of Natural Immunity in the Gut by Escherichia Coli Strain Nissle 1917," Nutr. Rev. 68:459-464 (2010); Grabig et al., "Escherichia Coli Strain Nissle 1917 Ameliorates Experimental Colitis Via Toll-Like Receptor 2- and Toll-Like Receptor 4-Dependent Pathways," Infect. Immun. 74:4075-4082 (2006), each of which is hereby incorporated by reference in its entirety)). These signals cause a variety of immunosuppressive effects that directly target the T-cells themselves (such as a decreased propensity to enter G2 or M phases of the cell cycle) (Trebichaysky et al., "Modulation of Natural Immunity in the Gut by Escherichia Coli Strain Nissle 1917," Nutr. Rev. 68:459-464 (2010), which is hereby incorporated by reference in its entirety) as well as attenuate immunostimulatory and inflammatory activities through decreased secretion of cytokines (IL-2 and IFN-γ) and costimulatory molecules (CD2 and CD28) (Trebichaysky et al., "Modulation of Natural Immunity in the Gut by Escherichia Coli Strain Nissle 1917," Nutr. Rev. 68:459-464 (2010), which is hereby incorporated by reference in its entirety). Direct immunosuppressive function is also upregulated by increased IL-10 secretion (Trebichaysky et al., "Modulation of Natural Immunity in the Gut by Escherichia Coli Strain Nissle 1917," Nutr. Rev. 68:459-464 (2010), which is hereby incorporated by reference in its entirety). FIG. 4B shows that by isolating the targeting and immunostimulatory potential of the EcN membrane from EcN's secretory immunosuppressive capabilities (Trebichaysky et al., "Modulation of Natural Immunity in the Gut by Escherichia Coli Strain Nissle 1917," Nutr. Rev. 68:459-464 (2010); Grabig et al., "Escherichia Coli Strain Nissle 1917 Ameliorates Experimental Colitis Via Toll-Like Receptor 2- and Toll-Like Receptor 4-Dependent Pathways," Infect. Immun. 74:4075-4082 (2006), each of which is hereby incorporated by reference in its entirety), and turning it into a bionanoparticle delivery device for the natural immunostimulatory milieu present in bacterial OMVs already (Grabig et al., "Escherichia Coli Strain Nissle 1917 Ameliorates Experimental Colitis Via Toll-Like Receptor 2- and Toll-Like Receptor 4-Dependent Pathways," Infect. Immun. 74:4075-4082 (2006), which is hereby incorporated by reference in its entirety), the normal immunosuppressive function of the probiotic bacteria is replaced with a powerful adjuvanting effect. Specifically, these EcN OMVs take advantage of TLR-2 and TLR-4 targeting directly to T-cells (top) described previously as well as supplemented targeting to antigen-presenting cells (APCs) such as macrophages (bottom). In addition to TLR-mediated phagocytosis, macrophage cell membranes additionally contain bactericidal/permeability-increasing protein (BPI) and LPS-binding protein to further enhance phagocytosis-inducing avidity of membranous flagellin, BPIs, and LPS that bacterial OMVs are naturally enriched with (Granoff, "Review of Meningococcal Group B Vaccines," Clin. Infect. Dis. 50:S54-S65 (2010); Trebichaysky et al., "Modulation of Natural Immunity in the Gut by Escherichia Coli Strain Nissle 1917," Nutr. Rev. 68:459-464 (2010); Grabig et al., "Escherichia Coli Strain Nissle 1917 Ameliorates Experimental Colitis Via Toll-Like Receptor 2- and Toll-Like Receptor 4-Dependent Pathways," Infect. Immun. 74:4075-4082 (2006); Zidek et al., "Decisive Role Lipopolysaccharide in Activating Nitric Oxide and Cytokine Production by the Probiotic *Escherichia Coli* Strain Nissle 1917," *Folia Microbiol.* 55:181-189 (2010), each of which is hereby incorporated by reference in its entirety). These interactions not only directly stimulate these immune cells through the binding event, but also facilitate delivery of a variety of immunostimulatory factors sensed intracellularly, such as TLR-4 and TRIF-activating LPS, heat-labile enterotoxin (LT), and outer-membrane lipids (Zidek et al., "Decisive Role Lipopolysaccharide in Activating Nitric Oxide and Cytokine Production by the Probiotic *Escherichia Coli* Strain Nissle 1917," *Folia Microbiol.* 55:181-189 (2010); Blasius and Beutler, "Intracellular Toll-Like Receptors," *Immunity* 32:305-315 (2010), each of which is hereby incorporated by reference in its entirety), and TLR-7 and TLR-9-activating "vita-PAMPs" (molecules that trick the immune cell into thinking a live pathogen is inside it) such as dsDNA, cytosolic mRNA, and bacterial proteases (Blasius and Beutler, "Intracellular Toll-Like Receptors," *Immunity* 32:305-315 (2010); Sander et al., "Detection of Prokaryotic mRNA Signifies Microbial Viability and Promotes Immunity," *Nature* 474:385-389 (2011), each of which is hereby incorporated by reference in its entirety). Taken together, the extracellular and intracellular immunostimulatory factors induce an enhanced inflammatory and generally immunoactivated state, which is spread to other immune cells through elevated IL-6, IL-12, IFN-γ, and TNF-α secretion, coupled with deceased IL-4 secretion (Granoff, "Review of Meningococcal Group B Vaccines," *Clin. Infect. Dis.* 50:S54-S65 (2010); Gizy et al., "The Probiotic *Escherichia Coli* Strain Nissle 1917 Induces Gammadelta T Cell Apoptosis Via Caspase- and FasL-Dependent Pathways," *Int. Immun.* 20: 829-840 (2008); Bickert et al., "Probiotic *Escherichia Coli* Nissle 1917 Suppresses Allergen-Induced Th2 Responses in the Airways," *Int. Arch. Allergy Immunol.* 149:219-230 (2009), each of which is hereby incorporated by reference in its entirety).

FIG. 6A shows dynamic light scattering hydrodynamic z-average particle sizes of both strains' OMVs. Formulations assessed in PBS. FIG. 6B shows GFP fluorescence-standardized ClyA-GFP (+) vaccine doses of EcJ and EcN OMVs were assayed for total protein content via BCA assay and normalized as a function of antigen content assayed by total fluorescence, demonstrating variable protein enrichment of the OMVs in a strain-dependent fashion. FIG. 6C shows the full protein profile of both EcJ and EcN OMVs via non-specific protein gel staining Outer membrane proteins characteristic of *E. coli* membrane fractions are noted. Ladder is given in kDa. FIG. 6D shows the OMV zeta potentials assessed in PBS. In FIG. 6A-6D, #no significant difference (P>0.05), *P<0.001, as determined by two-tailed Student's t-test. All values are given as mean+/-s.d.

FIG. 10A and FIG. 10C) and at the conclusion of the experiment post-boost (t=8 wk, FIG. 10B and FIG. 10D), from which T lymphocytes were isolated, restimulated, tagged for either IFN-γ (FIG. 10A-10B) or IL-10 (FIG. 10C-10D) expression, and analysed via FACS. PMA/Ionomycin was used as a positive-stimulation enhancing control. *P<0.001 determined by Tukey's HSD post-hoc test. All values are given as mean+/-s.d.

FIG. 12A shows the location of lpxM mutation site in the *E. coli* genome, located at 41.75 min. FIG. 12B shows dynamic light scattering hydrodynamic z-avg particle sizes of both OMVs. Formulations assessed in PBS. FIG. 12C shows GFP fluorescence-standardized ClyA-GFP(+) vaccine doses of EcJ and EcN OMVs assayed for total protein content via BCA assay. FIG. 12D shows western blot with anti-GFP antibodies of OMV suspensions from EcN cultures transformed with ClyA-GFP-containing plasmid. Background coloration altered to improve contrast. In FIG. 12B-12C*no statistically significant difference. All values are given as mean+/-s.d.

In FIG. 13A, BALB/c mice were injected subdermally on each ear with 10 μL of OMV solution. After 30 h, the mice were sacrificed and their ears were immediately resected and placed in 10% buffered formalin. Inflammopathology was rated on a scale of 1-5, 5 representing the greatest extent of effacement of normal tissue architecture by the inflammatory response. Each data point represents a representative frame taken from one ear section (n=6). In FIG. 13B, J774.1 murine macrophage culture was incubated for 12 h with protein content-standardized OMV doses, following which the culture media was collected and analyzed via ELISA for IL-6 content. *P<0.005, **P<0.0001 determined by Tukey's HSD post-hoc test. All values are given as mean+s.d.

FIG. 14A shows FACS analysis; FIG. 14B shows a summarizing graph. Masses given represent amount of OMVs added as determined by total protein content. All values are given as mean+/−s.d.

FIG. 18A-18B shows class-specific anti-74F antibody serum titers. FIG. 18C shows the ratio of serum titers of IgG1 to IgG2. FIG. 18D shows the proliferation index of antigen-restimulated spleen-derived T-cells harvested from end-point subjects, measured via CFSE stain. FIG. 18E-18F shows cytokine secretion levels from cultured, antigen-restimulated spleen-derived T-cells harvested from end-point subjects. Alum=Alhydrogel®. *P<0.005, **P<0.05 determined by Tukey's HSD post-hoc test. All values are given as mean+s.d.

FIG. 19A-19B shows class-specific anti-Arah2 antibody serum titers. FIG. 19C shows the ratio of serum titers of IgG1 to IgG2. FIG. 19D shows the proliferation index of antigen-restimulated spleen-derived T-cells harvested from end-point subjects, measured via CFSE stain. FIG. 19E-19F shows the cytokine secretion levels from cultured, antigen-restimulated spleen-derived T-cells harvested from end-point subjects. Alum=Alhydrogel®. *P<0.005, **P<0.05 determined by Tukey's HSD post-hoc test. All values are given as mean+s.d.

DETAILED DESCRIPTION OF THE INVENTION

Figure 1:
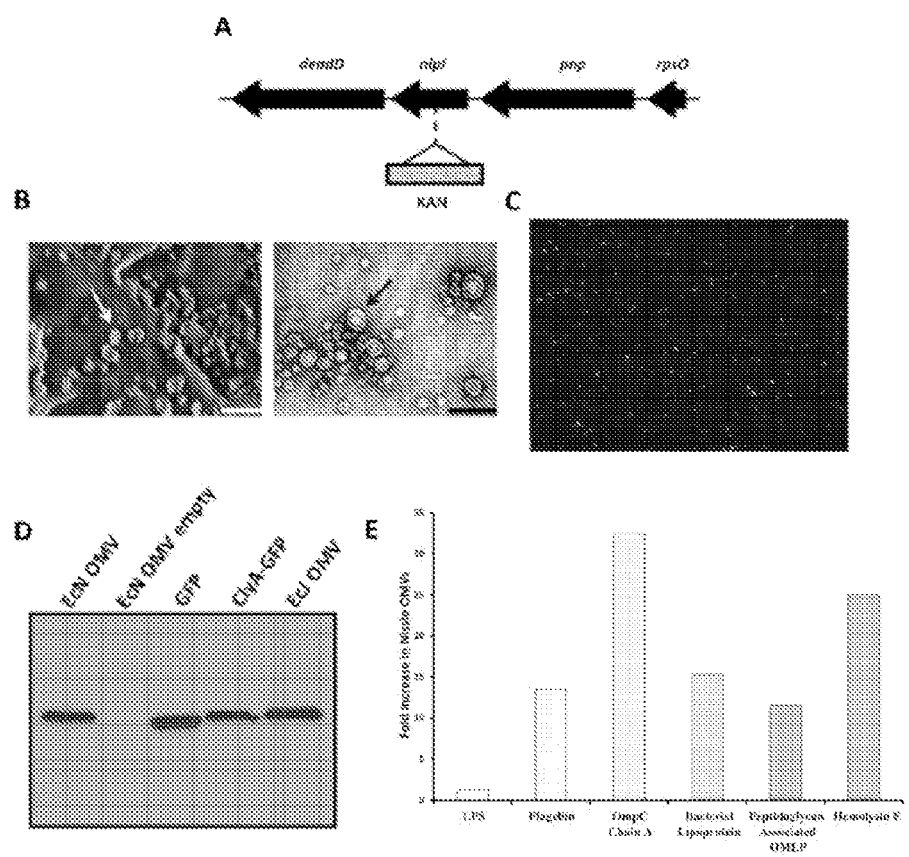
FIG. 1A-1E shows EcN nlpI mutant strain produces functional OMVs for recombinant subunit vaccine applications.

A first aspect of the present invention relates to a probiotic cell transformed with a construct suitable to overexpress and display on the surface of the probiotic cell a fusion protein comprising at least a portion of a transport protein coupled to at least a portion of one or more antigenic proteins or peptides.

As used herein, a "probiotic" refers to any organism, particularly microorganisms that exert a beneficial effect on the host animal such as increased health or resistance to disease. Probiotic organisms can exhibit one or more of the following non-limiting characteristics: non-pathogenic or non-toxic to the host; are present as viable cells, preferably in large numbers; capable of survival, metabolism, and persistence in the gut environment (e.g., resistance to low pH and gastrointestinal acids and secretions); adherence to epithelial cells, particularly the epithelial cells of the gastrointestinal tract; microbicidal or microbistatic activity or effect toward pathogenic bacteria; anticarcinogenic activity; immune modulation activity, particularly immune enhancement; modulatory activity toward the endogenous flora; enhanced urogenital tract health; antiseptic activity in or around wounds and enhanced would healing; reduction in diarrhea; reduction in allergic reactions; reduction in neonatal necrotizing enterocolitis; reduction in inflammatory bowel disease; and reduction in intestinal permeability.

As used herein, a "transport protein" refers to a protein normally present on the probiotic cell or probiotic-derived vesicle whose fusion to an antigenic protein or peptide allows display of that antigenic protein or peptide on the surface of the cell or vesicle.

The fusion proteins of the present invention can be generated as described herein or using any other standard technique known in the art. For example, the fusion polypeptide can be prepared by translation of an in-frame fusion of the polynucleotide sequences, i.e., a hybrid gene. The hybrid gene encoding the fusion polypeptide is inserted into an expression vector which is used to transform or transfect a host cell. Alternatively, the polynucleotide sequence encoding the transport protein is inserted into an expression vector in which the polynucleotide encoding the second polypeptide is already present. The second polypeptide or protein of the fusion protein can be fused to the N-, or preferably, to the C-terminal end of the transport protein.

Fusions between the transport protein and an antigenic protein or peptide may be such that the amino acid sequence of the transport protein is directly contiguous with the amino acid sequence of the second protein. Alternatively, the transport protein portion may be coupled to the second protein or polypeptide by way of a linker sequence such as the flexible 5-residue Gly linker described herein or the flexible linkers from an immunoglobulin disclosed in U.S. Pat. No. 5,516,637 to Huang et al, which is hereby incorporated by reference in its entirety. The linker may also contain a protease-specific cleavage site so that the second protein may be controllably released from the transport protein. Examples of protease sites include those specific to cleavage by factor Xa, enterokinase, collagenase, Igase (from *Neisseria gonorrhoeae*), thrombin, and TEV (Tobacco Etch Virus) protease.

Once the fusion protein is constructed, the nucleic acid construct encoding the protein is inserted into an expression system to which the molecule is heterologous. The heterologous nucleic acid molecule is inserted into the expression system or vector in proper sense (5'→3') orientation relative to the promoter and any other 5' regulatory molecules, and correct reading frame. The preparation of the nucleic acid constructs can be carried out using standard cloning methods well known in the art as described by Sambrook et al., Molecular Cloning: *A Laboratory Manual*, Cold Springs Laboratory Press, Cold Springs Harbor, N.Y. (1989), which is hereby incorporated by reference in its entirety. U.S. Pat. No. 4,237,224 to Cohen and Boyer, which is hereby incorporated by reference in its entirety, also describes the production of expression systems in the form of recombinant plasmids using restriction enzyme cleavage and ligation with DNA ligase.

Suitable expression vectors include those which contain replicon and control sequences that are derived from species compatible with the host cell. For example, if *E. coli* is used as a host cell, plasmids such as pUC19, pUC18 or pBR322 may be used.

Different genetic signals and processing events control many levels of gene expression (e.g., DNA transcription and messenger RNA ("mRNA") translation) and subsequently the amount of fusion protein that is displayed on the cell or vesicle surface. Transcription of DNA is dependent upon the presence of a promoter, which is a DNA sequence that directs the binding of RNA polymerase, and thereby promotes mRNA synthesis. Promoters vary in their "strength" (i.e., their ability to promote transcription). For the purposes of expressing a cloned gene, it is desirable to use strong promoters to obtain a high level of transcription and, hence, expression and surface display. Depending upon the host system utilized, any one of a number of suitable promoters may be used. For instance, when using E coil, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV 5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Translation of mRNA in prokaryotes depends upon the presence of the proper prokaryotic signals, which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference in its entirety.

Following transformation of the host cell with an expression vector comprising the nucleic acid construct encoding the fusion protein, the fusion protein is expressed and displayed on the cell surface as well as the surface of outer membrane vesicles.

In one embodiment of the present invention, a plurality of proteins or polypeptides are displayed on the surface of a plurality of cells or cell vesicles. The plurality of proteins or polypeptides displayed on the cell or cell vesicle surface are fusion proteins where each fusion protein has a different second protein. The plurality of fusion proteins forms a library of proteins or peptides that are amenable to cell or cell vesicle surface display.

In one embodiment, the probiotic cell is mutated to hyperexpress vesicles containing the fusion protein.

As used herein, "vesicles" refers to outer membrane vesicles, also known as blebs, which are vesicles formed or derived from fragments of the outer membrane of gram negative bacterium naturally given off during growth.

Mutations associated with increased vesicle production are known in the art (McBroom and Kuehn, "Release of Outer Membrane Vesicles by Gram-Negative Bacteria is a Novel Envelope Stress Response," *Mol. Microbiol.* 63: 545-558 (2007), which is hereby incorporated by reference in its entirety). For example, disruptions in the nlpI, degS, degP, tolB, pal, rseA, tolA, ponB, tatC, ompR, wzxE, ompC, yieM, pnp, and wag genes have all been shown to result in overproduction of vesicles.

In another embodiment, the transport protein is an adhesin, immunomodulatory compound, protease, or toxin. Examples of such proteins, which have been shown to be associated with bacterial membranes as well as outer membrane vesicles include, without limitation, ApxI, leukotoxin, heat labile enterotoxin, Shiga toxin, ClyA, VacA, OspA and OspD, Haemagglutinin, peptidoglycan hydrolase, phospholipase C, hemolysin, alkaline Phosphatase, Arg-gingipain, Lys gingipain, IpaB, IpaC, IpaD, dentilisin, chitinase, bacteriocin, adhesin, and pore-forming toxin (Keuhn and Kesty, "Bacterial Outer Membrane Vesicles and the Host-Pathogen Interaction," *Genes & Development* 19: 2645-2655 (2005), which is hereby incorporated by reference in its entirety). In a preferred embodiment, the transport protein is ClyA.

The antigenic protein or peptide may be any antigenic protein or peptide known in the art, but preferably is derived from pathogenic bacterial, fungal or viral organisms, *Streptococcus* species, *Candida* species, *Brucella* species, *Salmonella* species, *Shigella* species, *Pseudomonas* species, *Bordetella* species, *Clostridium* species, Norwalk virus, *Bacillus anthracis*, *Mycobacterium tuberculosis*, human immunodeficiency virus (HIV), *Chlamydia* species, Human Papillomaviruses, Influenza virus, Paramyxovirus species, Herpes virus, Cytomegalovirus, Varicella-Zoster virus, Epstein-Barr virus, Hepatitis viruses, *Plasmodium* species, *Trichomonas* species, sexually transmitted disease agents, viral encephalitis agents, protozoan disease agents, fungal disease agents, bacterial disease agents, cancer cells, or combinations.

Also in the accordance with this aspect of the present invention, the probiotic-derived vesicle may be isolated from any known probiotic cell in the art. In a preferred embodiment, the probiotic cell is selected from the group consisting of *Bifidobacterium longum*, *Bifidobacterium lactis*, *Bifidobacterium animalis*, *Bifidobacterium breve*, *Bifidobacterium infantis*, *Bifidobacterium adolescentis*, *Lactobacillus acidophilus*, *Lactobacillus casei*, *Lactobacillus paracasei*, *Lactobacillus salivarius*, *Lactobacillus reuteri*, *Lactobacillus rhamnosus*, *Lactobacillus johnsonii*, *Lactobacillus plantarum*, *Lactobacillus fermentum*, *Lactococcus lactis*, *Streptococcus thermophilus*, *Lactococcus lactis*, *Lac-*

*tococcus diacetylactis, Lactococcus cremoris, Lactobacillus bulgaricus, Lactobacillus helveticus, Lactobacillus delbrueckii, Escherichia coli,* and mixtures thereof. In a preferred embodiment, the probiotic cell is *Escherichia coli* Nissle.

In accordance with this embodiment, the fusion protein comprises at least a portion of a ClyA protein coupled to at least a portion of one or more antigenic proteins or peptides. Suitable ClyA proteins and nucleic acid molecules encoding them are described in U.S. Patent Application Publication No. 2010/0233195 A1 to DeLisa et al., which is hereby incorporated by reference in its entirety.

Another aspect of the present invention is directed to a method of eliciting an immune response in a mammal, said method comprising providing the probiotic cell described above, and administering the probiotic cell to the mammal under conditions effective to elicit the immune response.

In accordance with this and all other aspects of the present invention, the term "immune response" refers to the development in a subject of a humoral and/or a cellular immune response to an antigen present in the composition of interest. A "humoral immune response" refers to an immune response mediated by antibody molecules, while a "cellular immune response" is one mediated by T-lymphocytes and/or other white blood cells. The antigen of interest may also elicit an antibody-mediated immune response. Hence, an immunological response may include one or more of the following effects: the production of antibodies by B-cells; and/or the activation of suppressor, cytotoxic, or helper T-cells and/or T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

The probiotic cell can be administered to the mammal using methods known in the art including parenteral, topical, intravenous, oral, subcutaneous, intraperitoneal, intranasal or intramuscular means. The most typical route of administration for compositions formulated to induce an immune response is subcutaneous although others can be equally as effective. The next most common is intramuscular injection. This type of injection is most typically performed in the arm or leg muscles. Intravenous injections as well as intraperitoneal injections, infra-arterial, intracranial, or intradermal injections are also effective in generating an immune response.

The probiotic cell of the present invention may be formulated for parenteral administration. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the pharmaceutical agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices such as those described by Medtronic, Northridge, Calif. Such devices allow continuous infusion of desired compounds avoiding multiple injections and multiple manipulations.

In addition to the formulations described previously, the compositions of the present invention may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

Detection of an effective immune response may be determined by a number of assays known in the art. For example, a cell-mediated immunological response can be detected using methods including, lymphoproliferation (lymphocyte activation) assays, CTL cytotoxic cell assays, or by assaying for T-lymphocytes specific for the antigen in a sensitized subject. Such assays are well known in the art.

The presence of a humoral immunological response can be determined and monitored by testing a biological sample (e.g., blood, plasma, serum, urine, saliva feces, CSF or lymph fluid) from the mammal for the presence of antibodies directed to the immunogenic component of the administered polymerized product. Methods for detecting antibodies in a biological sample are well known in the art, e.g., ELISA, Dot blots, SDS-PAGE gels or ELISPOT. The presence of a cell-mediated immunological response can be determined by proliferation assays ($CD4^+$ T cells) or CTL (cytotoxic T lymphocyte) assays which are readily known in the art.

Effective doses of the probiotic cells of the present invention, for the induction of an immune response, vary depending upon many different factors, including means of administration, target site, physiological state of the mammal, whether the mammal is human or an animal, other medications administered, and whether treatment is prophylactic or therapeutic. Usually, the subject is a human, but in some diseases, such the subject can be a nonhuman mammal, such as a bovine. Other non-human mammals amenable to treatment in accordance with the methods of the present invention include primates, dogs, cats, rodents (e.g., mouse, rat, guinea pig), horses, deer, cervids, cattle and cows, sheep, and pigs. Treatment dosages need to be titrated to optimize safety and efficacy, and could involve oral treatment.

In one embodiment of this aspect of the present invention, the probiotic cell is mutated to hyperexpress vesicles containing the fusion protein. Methods for mutating a probiotic cell for this purpose are described above.

The transport protein can be an adhesin, immunomodulatory compound, protease, or toxin. Examples of proteins which may be used as transport proteins are described above. Preferably, the transport protein is ClyA.

In preferred embodiments, the antigenic protein or peptide and the probiotic cell are derived and/or selected from the groups described above. In a more preferred embodiment, the probiotic cell is *Escherichia coli* Nissle.

The present invention is also directed to a probiotic-derived vesicle displaying a fusion protein, wherein said fusion protein comprises at least a portion of a transport protein coupled to at least a portion of one or more antigenic proteins or peptides.

The probiotic-derived vesicle is first prepared using the methods described above for generating the transformed probiotic cell. Outer membrane vesicles resulting from the probiotic cell overexpressing and displaying the fusion protein will also display said fusion protein. These outer membrane vesicles can be prepared in various ways. Methods for obtaining suitable preparations are disclosed in, for instance, the references cited herein. Techniques for forming OMVs include treating bacteria with a bile acid salt detergent e.g. salts of lithocholic acid, chenodeoxycholic acid, ursodeoxycholic acid, deoxycholic acid, cholic acid, and ursocholic acid. Other techniques may be performed substantially in the absence of detergent using techniques such as sonication, homogenisation, microfluidisation, cavitation, osmotic shock, grinding, French press, blending, etc (see WO2004/019977).

A preferred method for OMV preparation involves ultrafiltration instead of high speed centrifugation on crude OMVs (see WO2005/004908). This allows much larger amounts of OMV-containing supernatant to be processed in a much shorter time (typically >15 liters in 4 hours).

The transport protein displayed on the vesicle may be any protein known in the art to be expressed on the surface of a vesicle. In a preferred embodiment, the transport protein is an adhesin, immunomodulatory compound, protease, or toxin. Exemplary proteins from these categories have been described above. More preferably, the transport protein is ClyA.

The antigenic protein or peptide and probiotic cells are discussed above.

In another preferred embodiment, the probiotic-derived vesicle from *Escherichia coli* Nissle displays a fusion protein comprising at least a portion of a ClyA protein coupled to at least a portion of one or more antigenic proteins or peptides.

A further aspect of the present invention relates to a method of eliciting an immune response in a mammal, said method comprising providing the probiotic-derived vesicle described above and administering the probiotic-derived vesicle to the mammal under conditions effective to elicit the immune response.

Methods for preparing cellular vesicles suitable for administration as drug and vaccine delivery vehicles and methods for formulations for administration of cellular vesicles are known in the art and described above and in WO2002/0028215 to Kadurugamuwa and Beveridge, WO2006/024946 to Oster et al., and WO2003/051379 to Foster et al., which are hereby incorporated by reference in their entirety.

As described above, the transport protein is preferably an adhesin, immunomodulatory compound, protease, or toxin. In a more preferred embodiment, the transport protein is ClyA.

Examples and preferred embodiments of the antigenic protein or peptide as well as the probiotic cell are also described above.

Another aspect of the present invention is directed to a probiotic cell transformed with a construct suitable to overexpress and display on the surface of the probiotic cell a fusion protein comprising at least a portion of a transport protein coupled to at least a portion of one or more antigenic food allergy proteins or peptides.

The transformed probiotic cell, fusion protein, as well as methods of generating them, are described above.

The most common food allergy proteins are derived from milk, eggs, fish, crustacean shellfish, tree nuts, peanuts, wheat, coconut, and soybeans. Examples of specific food allergy proteins include, but are not limited to, the following: milk (Bosd4, Bosd5, and Bosd6), eggs (ovomucoid, ovalbumin, ovotransferrin, lysozyme, and alpha-livetin), fish (Gadm1, Gadm2, Gadm3, Sals1, Sals2, Sals3, Gadc1, and Xipg1), crustacean shellfish (Homa1, Homa3, Homa6, Penm1, Penm2, Penm3, Penm4, Penm6, Litv1, Litv2, Litv3, Litv4, and Chaf1), tree nuts (Prudu3, Prudu4, Prudu5, Prudu6, Jugn1, Jugn2, Jugr1, Jugr2, Bere2, Bere1, Cass5, Cora 1.0401, Cora 1.0402, Cora 1.0403, Cora 1.0404, Cora11, Cora8, Cora9, Anah1, pecan protein albumin 2S, and Litc1), peanuts (Arah1, Arah2, Arah3, Arah4, and Arah5), wheat (Tria12, Tria14, Tria18, and Tria19), coconut (CNP1), and soybeans (Glym1, Glym2, Glym3, Glym4, and Glym5). In one embodiment, the food allergy is to peanuts and the antigenic food allergy protein or peptide is Arah2, which is a protein from peanuts.

The present invention is further directed to a probiotic-derived vesicle displaying a fusion protein, wherein said fusion protein comprises at least a portion of a transport protein coupled to at least a portion of one or more antigenic food allergy proteins or peptides.

The probiotic-derived vesicle, fusion protein, as well as methods of generating them, are described above.

The present invention is also directed to a method of immunizing a subject against a food allergy, said method comprising selecting a subject having a food allergy, providing the probiotic cell described above, or, in another embodiment, the probiotic-derived vesicle described above, and administering the probiotic-derived vesicle to the selected subject under conditions effective to immunize the subject against the food allergy.

A subject having a food allergy may be selected based upon previous allergy testing methods including skin prick testing, blood tests, and food challenges. Additional diagnostic tools for food allergy include endoscopy, colonoscopy, and biopsy. In a preferred embodiment, the selected subject has a peanut allergy.

Modes of formulation and administration in accordance with this method are described above.

Another aspect of the present invention involves a probiotic cell transformed with a construct suitable to overexpress and display on the surface of the probiotic cell a fusion protein comprising at least a portion of a transport protein coupled to at least a portion of one or more antigenic viral proteins or peptides The transformed probiotic cell, fusion protein, as well as methods of generating them are described above.

In accordance with this aspect of the present invention, antigenic viral proteins or peptides may be derived from, but not limited to, the following viruses: Human Immunodeficiency Virus (HIV) (p24, gp120, and gp40), influenza A virus (HA and NA), influenza B virus (HA and NA), influenza C virus (HA and NA), rabies virus Glycoprotein G), vesicular stomatitis virus, respiratory syncytial virus, measles virus, parainfluenza virus, mumps virus, yellow fever virus, west nile virus, dengue virus (CPC, MPM, and EPE), rubella virus, sindbis virus, semliki forest virus, ross river virus, rotavirus, parvovirus, JC polyoma virus, BK polyoma virus, Human papillomavirus (HPV), adenovirus, hepatitis B virus, hepatitis C virus (E1 and E2), hepatitis A virus, hepatitis E virus, Human herpesvirus, vaccinia virus, monkeypox virus, cowpox virus, human T-cell leukemia virus, coxsackie virus, polio virus, rhinovirus (VP1-3), enterovirus, echovirus, ebola virus (GP1 and GP2), coronavirus (CoV-N, CoV-S, CoV-M, CoV-E), variola virus, hantaan virus, adeno-associated virus, astrovirus, hendra virus, lassa virus, nipah virus, Marburg virus (NPC1, GP1,2), and Norwalk virus. In one embodiment, the antigenic viral protein or peptide is H1N1 hemagglutinin.

The present invention also involves a probiotic-derived vesicle displaying a fusion protein, wherein said fusion protein comprises at least a portion of a transport protein coupled to at least a portion of one or more antigenic viral proteins or peptides.

The probiotic-derived vesicle, fusion protein, as well as methods of generating them are described above.

Another aspect of the present invention involves a method of immunizing a subject against a viral infection, said method comprising selecting a subject at risk of developing a viral infection, providing the probiotic cell described above, or, in another embodiment, the probiotic-derived vesicle described above, and administering the probiotic cell or probiotic-derived vesicle to the selected subject under conditions effective to immunize the subject the viral infection.

A subject at risk of developing a viral infection may be a subject that has a reduced or suppressed immune system (e.g., due to a disease, condition, or treatment, or a combination thereof. Other at risk subjects may include children, the elderly, as well as hospital workers. In a preferred embodiment, the viral infection is influenza.

Modes of formulation and administration in accordance with this method are described above.

Yet another aspect of the present invention is directed to a probiotic cell transformed with a construct suitable to overexpress and display on the surface of the probiotic cell a fusion protein comprising at least a portion of a transport protein coupled to at least a portion of one or more antigenic intracellular bacterial proteins or peptides.

The transformed probiotic cell, fusion protein, as well as methods of generating them, are described above.

Antigenic intracellular bacterial proteins or peptides may be derived from, but not limited to, intracellular pathogens such as *Chlamydophila, Ehrlichia, Rickettsia, Mycobacterium, Brucella, Francisella, Legionella*, and *Listeria*. Examples of specific antigenic proteins or peptides include, but are not limited to, the following: *Chlamydophila* (MOMP, omp2, Cpj0146, Cpj0147, Cpj0308), *Ehrlichia* (P28 outer membrane protein and hsp60), *Mycobacterium* (Ag85 complex, MPT32, Phos, Dnak, GroES, MPT46, MPT53, MPT63, ESAT-6 family, MPT59, MAP 85A, MAP 85B, SOD, and MAP 74F), *Brucella* (BMEII0318, BMEII0513, BMEII10748, BMEII1116, BP26, and omp31), *Francisella* (O-antigen), *Legionella* (Mip, LPS, outer membrane protein), and *Listeria* (IspC, lemA, and listeriolysin O). In one embodiment, the antigenic protein or peptide is 74F protein, which is from *Mycobacterium* paratuberculosis, the causative agent of Johne's disease in ruminants.

The present invention also relates to a probiotic-derived vesicle displaying a fusion protein, where said fusion protein comprises at least a portion of a transport protein coupled to at least a portion of one or more antigenic intracellular bacterial proteins or peptides.

The probiotic-derived vesicle, fusion protein, as well as methods of generating them, are described above.

A final aspect of the present invention is directed to a method of immunizing a mammal against an intracellular bacterial infection, said method comprising selecting a mammal at risk of developing an intracellular bacterial infection providing the probiotic cell described above, or, in another embodiment, the probiotic-derived vesicle described above, and administering the probiotic cell or probiotic-derived vesicle to the selected animal under conditions effective to immunize the animal against the intracellular bacterial infection.

Modes of formulation and administration in accordance with this method are described above.

A mammal may be at risk of developing an intracellular bacterial infection if the mammal has a reduced or suppressed immune system (e.g., due to a disease, condition, or treatment, or a combination thereof). Mammals, such as ruminants, are also at risk due to living in herds. In preferred embodiments, the mammal is a ruminant and the intracellular bacterial infection is Johne's disease.

EXAMPLES

The following examples are provided to illustrate embodiments of the present invention but they are by no means intended to limit its scope.

Materials and Methods for Examples 1-4

Preparation of OMVs.

OMVs were purified in accordance with a previously established procedure (Valderrama-Rincon et al., "An Engineered Eukaryotic Protein Glycosylation Pathway in *Escherichia Coli*," *Nat. Chem. Biol.* 8:434-436 (2012), which is hereby incorporated by reference in its entirety). Briefly, plasmid pBAD-ClyA-GFP, containing an arabinose promoter, was transformed into *E. coli* vesicle-overproducing strains JC8031 (Baba et al., "Construction of *Escherichia Coli* K12 In-Frame, Single-Gene Knockout Mutants: the Keio Collection," *Mol. Syst. Biol.* 2:68 (2006), which is hereby incorporated by reference in its entirety), JH1, and JH1-LpxM, and selected in LB-chloramphenicol or LB-kanamycin medium, respectively. Flasks containing 250 mL of medium were inoculated with overnight culture and allowed to grow at 37° C. and 230 rpm until the $OD_{600}$ reached ~0.5. Protein expression was induced at this point by addition of L-arabinose to a final concentration of 0.2%. Cell-free culture supernatants were collected 12 hours after induction (following centrifugation at 5000 g for 15 min) and then filtered through a 0.45 μm filter. Vesicles were isolated by ultracentrifugation (Beckman-Coulter; Ti SW28 rotor, 26000×g, 3 h, 4° C.) and resuspended in PBS.

Microscopy.

Scanning electron microscopy was conducted on purified vesicles flash-frozen on copper wafers in nitrogen slush and viewed in a LEO 1550 FESEM. Transmission electron microscopy was conducted on purified vesicles negatively stained with 2% uranyl acetate on 400-mesh Formvar carbon-coated copper grids and viewed in a FEI Tecnai F20 TEM. Fluorescence microscopy was conducted on purified vesicles suspended in PBS that were placed on a glass slide, sealed with a coverslip, and examined using an Olympus BX41 microscope with a GFP filter set.

Protein Analyses.

Protein concentrations in OMV and purified recombinant protein preparations (used as controls in the vaccine study) were quantified by the bicinchoninic-acid assay (BCA Protein Assay; Pierce) using BSA as the protein standard. Fluorescence of GFP in protein and OMV samples was measured in a microplate spectrofluorometer (Gemini EM; Molecular Devices) using excitation and emission wavelengths of 481 nm and 507 nm, respectively (Miller, "Experiments in Molecular Genetics," Cold Spring Harbor Laboratory Press, U.S. (1972), which is hereby incorporated by reference in its entirety). For SDS/PAGE, samples were prepared in sample-loading buffer containing β-mercaptoethanol and heated at 90° C. for 10 min before electrophoresis on 10% polyacrylamide gels. Proteins were transferred to polyvinylidine difluoride membranes for Western blot analysis and probed with monoclonal mouse anti-GFP IgG (Invitrogen; 1:2000) primary antibody, and horseradish peroxidase conjugated goat anti-mouse IgG (Jackson Immunoresearch; 1:10000) secondary antibody. Membranes were developed by autoradiography with ECL detection reagents (GE Healthcare).

LPS Analyses.

Bacterial LPS concentrations were determined by measuring the presence of KDO according to a previously described colorimetric assay (Kolling and Matthews, "Export of Virulence Genes and Shiga Toxin by Membrane Vesicles of *Escherichia Coli* 0157:H7," *Appl. Environ. Microbiol.* 65:1843-1848 (1999); Bernadac et al., "*Escherichia Coli* Tol-Pal Mutants Form Outer Membrane Vesicles," *J. Bacteriol.* 180:4872-4878 (1998), each of which is hereby incorporated by reference in its entirety). Briefly, OMV samples (50 μL) in PBS were combined with 0.2 M $H_2SO_4$ (5 μL) and heated at 100° C. for 20 min. The samples were cooled to room temperature for 5 min, and then 25 μL of 0.04 M $NaIO_4$ was added to the mixture and thoroughly mixed by pipeting. After 20 min of incubation at room temperature, 2% $NaAsO_2$ (65 μL) was added to the sample tubes, and the samples were vortexed until the characteristic yellow color disappeared. Thiobarbituric acid (0.3%, 250 μL) was added, and the samples were returned to 100° C. for 10 min, followed by the immediate addition of dimethyl sulfoxide (125 μL) and thorough mixing by pipeting. The samples were cooled to room temperature for 5 min, and the absorbance was read at 550 nm in a microplate spectrophotometer (Molecular Devices). Calibration standards were prepared from KDO ammonium salt (Sigma-Aldrich).

Dynamic Light Scattering.

Dynamic light scattering measurements were performed with the Nanosizer Nano ZS (Malvern Instruments) using Dispersion Technology Software version 4.20 for data acquisition and analysis. OMV samples contained 100 μg/mL total protein in 1 mL of PBS. The refractive index and viscosity of water (1.333 and 0.890 cP) were used as model parameter inputs.

Recombinant Protein Purification.

Cultures of *E. coli* DH5α transformed with pBAD-ClyA-GFP-His, pBAD-ClyA-His, or pBAD-GFP-His were grown in 100 mL of LB medium containing chloramphenicol. Protein expression was induced by the addition of L-arabinose to a final concentration of 0.2% after the $OD_{600}$ reached ~0.5. Bacterial cultures were harvested 4 hours after induction by centrifugation (5000 g, 15 min) and lysed by treatment with lysozyme (1 mg/mL) and Triton X-100 (1% vol/vol). The polyhistidine-tagged proteins in the soluble fraction were purified by immobilized-metal affinity chromatography (Ni-NTA Agarose; Qiagen) according to the manufacturer's instructions. The proteins were eluted with 200 mM imidazole in a buffer containing 50 mM $NaH_2PO_4$ and 300 mM NaCl (pH 8.0), and they were subsequently desalted into PBS using PD-10 size exclusion chromatography columns (Amersham Biosciences).

Cell Isolation and Culture.

Mouse red blood cells (MRBCs) were extracted via post-euthanasia cardiac puncture into EDTA, centrifuged (2000 rpm, 15 min) and separated from plasma and the buffy coat, then washed in PBS and stored at 4° C. as a 10% solution (w/v). For bone marrow-derived macrophages and dendritic cells (DCs), bone marrow was obtained from mouse femurs and grown for 6 to 8 days in RPMI 1640 in the presence of 10% L929 conditioned medium (Cormack et al., "FACS-Optimized Mutants of the Green Fluorescent Protein," *Gene* 173:33-38 (1996), which is hereby incorporated by reference in its entirety) and collected 7 days later by scraping. Bone marrow-derived DCs were cultured in the presence of 20 ng/ml GM-CSF and collected 6-8 days after culture (Carlo and Jackson, "A New and Improved Microassay to Determine 2-Keto-3-Deoxyoctonate in Lipopolysaccharide of Gram-Negative Bacteria," *Anal. Biochem.* 601: 595-601 (1978), which is hereby incorporated by reference in its entirety). For the splenic T-cells and B-cells, spleens were harvested, mechanically homogenized, and filtered through a 100 μm cell strainer (Falcon). Erythrocytes were lysed with cold ACK lysing buffer (Cellgro) for 5 min, and the cell suspension was washed with complete medium. T cells were purified with negative selection enrichment columns (R&D Systems) following the manufacturer's recommendations. B cells were enriched by negative selection using magnetic isolation kits, as per manufacturer's instructions (Miltenyi Biotec). This resulted in cell purities of >97% as determined by flow cytometry.

ELISA.

Polystyrene microtiter 96-well plates (Maxisorp; Nunc Nalgene) were coated with GFP (5 μg/ml in carbonate buffer, pH 9.6) and incubated overnight at 4° C. Plates were blocked with 3% BSA in PBS containing 0.05% Tween-20 (PBST). Samples were serially diluted 2-fold in blocking buffer in a range of 1:200-204, 800, added to the wells, and incubated for 2 hours at 37° C. Plates were washed six times with PBST, and biotinilated goat anti-mouse IgG, IgM (Sigma), or monoclonal IgG1 or IgG2 (BD Pharmingen) were added to the wells (1 μg/ml) for 1 hour at 37° C. Avidin-horseradish peroxidase (1:1000; Sigma) was then added and incubation continued for 30 min at 37° C. After six additional washes with PBST, 3,3',5,5' tetramethylbenzidine substrate (1-Step TMB; Pierce) was added, and the enzyme reaction proceeded for 20 min. The reaction was stopped with 2 M $H_2SO_4$. The absorbance was quantified in a microplate spectrophotometer at a wavelength of 450 nm. Serum antibody titers were determined by measuring the last dilution that resulted in three standard deviations above background. For the determination of cytokines, cells were resuspended at a concentration of $2 \times 10^6$ cells/well in medium RPMI 1640 (supplemented with FCS and antibiotics), seeded into 96-well plates and incubated for 48 h with 5 μg GFP. Cytokine levels were measured in the supernatants by using standard ELISA kits (eBioscience).

Hemagglutination Inhibition Assays.

Samples of A/PR8/34 and X31 influenza virus were inactivated in 0.02% formalin for 18 h at 37° C., and then dialyzed against PBS at room temperature overnight. Each virus sample was titered for stock hemagglutination units (HAs) as described elsewhere (Cottey et al., "Influenza Virus," *Curr. Protoc. Immunol.* (2001), which is hereby incorporated by reference in its entirety) using serial two-fold dilutions of virus into freshly-drawn 1% MRBCs in PBS. Subsequently, serial two-fold dilutions of serum from appropriately vaccinated mice were incubated as described elsewhere (Cottey et al., "Influenza Virus," *Curr. Protoc. Immunol.* (2001), which is hereby incorporated by reference in its entirety) with 4 HA diluted virus samples and then exposed to 1% MRBCs in PBS. Both assays were read using the teardrop method to determine the cut-off between hemagglutination and hemagglutination absence/inhibition.

Cytokine Expression Analyses.

For splenic lymphocytes, cells were stimulated overnight with 5 µg/ml GFP, 5 ng/ml IL-2 and 10 µg/ml anti-CD28, and then cultured with brefeldin A. Cells were stained with fluorescent antibodies against the surface markers CD3 (clone 17A2) and CD4 (clone RM4-5), permeabilized, fixed and incubated with antibodies against the cytokines IFN-γ (clone XMG1.2) or IL-10. All incubations were carried out on ice for 30 min. All antibodies were purchased from BD Bioscience or eBioscience. For each sample, at least 50,000 cells were analyzed. The data were collected and analyzed using CELLQuest or FlowJo software and a FACScalibur flow cytometer (Becton Dickinson, San Jose, Calif.). For macrophages, cells were plated as above and also incubated with increasing concentrations of OMVs. Sixteen hours later, brefeldin A (10 µg/ml) was added and cells were incubated for 6 additional hours. DCs were then collected to be stained and analyzed by flow cytometry. Prior to staining, cells were incubated with an anti-Fcγ III/II receptor (BD Biosciences) and 10% normal mouse serum (NMS) in PBS containing 0.1% BSA, 0.01% $NaN_3$. Cells were stained with antibodies against the surface marker CD11c (clone 223H7), fixed in 2% paraformaldehyde, permeabilized with saponin and then incubated with fluorescent antibodies against the cytokines IL-12p40/p70 (clone C17.8), IL-10 (clone JES5-16E3) or IL-4 (clone 11B11). Incubations were carried out for 30 min on ice. All antibodies were purchased from BD Biosciences or eBioscience. Data was collected and analyzed as described above.

Inflammopathology.

Four groups of three 8-week old BALB/c mice (Charles River Laboratories) each were injected s.d. in each ear with 10% of the vaccine dosage described previously for PBS, EcJ OMVs, EcN OMVs, and EcN-LpxM OMVs. Mice were euthanized 30 hours after injection, and their ears were resected and immediately fixed in 10% formalin. Tissue samples were processed routinely for histopathology and stained with hematoxylin and eosin for light microscopic evaluation. Slides were read and graded in a blinded fashion by a licensed pathologist. Changes were given an overall score based on the grade of inflammation, edema, and tissue damage/remodeling as well as the presence or absence of vasculitis or vascular thrombi.

Phagocytosis Assay.

Bone marrow-derived macrophages were plated in 6-well plates ($10^6$/well) for 16 hours and incubated with increasing concentrations of ClyA-GFP(+) EcN or EcJ OMVs. Two hours after the addition of the OMVs, plates were washed vigorously; cells were collected and analyzed by flow cytometry to detect internalized GFP. The data were collected using a FACScalibur flow cytometer and analyzed in CELLQuest software (Becton Dickinson, San Jose, Calif.). For each sample, at least 30,000 cells were analyzed.

T-Cell Activation Analyses.

T-cell activation by stimulated DCs was assayed as described previously (Herlax et al., "Role of Lipopolysaccharide on the Structure and Function of Alpha-Hemolysin From *Escherichia Coli*," *Chem. Phys. Lipids* 135:107-115 (2005); Noss et al., "Toll-Like Receptor 2-Dependent Inhibition of Macrophage Class II MHC Expression and Antigen Processing by 19-kDa Lipoprotein of *Mycobacterium Tuberculosis*," *J. Immunol.* 167:901-918 (2001), each of which is hereby incorporated by reference in its entirety). Briefly, 96-well plates were incubated overnight with 10 µg/mL anti-mouse CD3 (clone 145-2C11; BD Biosciences) at 4° C., after which plates were washed 3 times with complete RPMI. T cells were then labeled with CFSE as described and seeded into wells from at $2 \times 10^5$ cell/well. T-cells were co-incubated with $4 \times 10^4$ cell/well DCs, 5 µg/mL anti-mouse CD28 (clone 37.51, Biolegend), and 1-100 µg/mL EcJ or EcN OMVs. Samples prepared for flow cytometry analysis incubated for 48 h at 37° C., incubated for 4-6 h with 25 ng/mL PMA, 1 µg/mL ionomycin, and 10 µg/mL brefeldin A, and then were collected and stained with IFN-γ and IL-10 (eBiosciences). Samples prepared for ELISA analysis of culture supernatants were also incubated for 48 h at 37° C. Samples prepared for proliferation analysis were incubated at 37° C. for 7 days, then trypsinized and analyzed by flow cytometry for loss of CFSE staining.

Design of Nissle nlpI-Mutant JH1 and lpxM Mutant JH1-LpxM.

nlpI and lpxM mutations were generated using P1 transduction of the nlpI::kan and lpxM::kan alleles, creating strains JH1 (ΔnlpI) and JH1-LpxM (ΔnlpIΔlpxM), from the Keio collection (Baba et al., "Construction of *Escherichia coli* K12 In-Frame, Single-Gene Knockout Mutants: The Keio Collection," *Mol. Syst. Biol.* 2:68 (2006), which is hereby incorporated by reference in its entirety). Briefly, *E. coli* Nissle 1917 bacteria were grown overnight and incubated with P1 lysates from appropriate Keio single mutants, as described elsewhere (Miller, J. *Experiments in Molecular Genetics*, Cold Spring Harbor Laboratory Press, U.S. (1972), which is hereby incorporated by reference in its entirety). Transduction was performed using 50 mM $CaCl_2$ for 20 min at 37° C. and 1 M Na-citrate for 40 min at room temp, and selective plating was done using medium containing 20 mM Na-citrate. Visual characterization was conducted using a LEO 1550 FESEM, a FEI Tecnai F20 TEM, and an Olympus BX41 for SEM, TEM, and fluorescent microscopy, respectively. Further protein characterization was conducted using BCA assay and Western blot, while LPS was analyzed using a KDO colorimetric assay and proteomics were conducted using the isobaric tag for relative and absolute quantitation, or iTRAQ, method.

Mouse Immunizations.

Ten groups of ten 8-week old BALB/c mice (Charles River Laboratories) each were immunized s.c. with 100 µL of PBS containing purified protein or OMV preparations as described. The ten treatment groups were immunized with, respectively: PBS, 2.5 µg GFP/H1N1 HA, 2.5 µg ClyA, 2.5 µg GFP and ClyA mixture, 2.5 µg ClyA-GFP/H1N1 HA fusion, 2.5 µg alum and ClyA-GFP/H1N1 HA mixture (Alyhydrogel®, 1.3% aluminum hydroxide [mass:volume]), and recombinant fluorescent equivalents of EcJ+ClyA-GFP/H1N1 HA, EcJ (empty), EcN+ClyA-GFP/H1N1 HA, and EcN (empty). Two doses of vaccine (priming dose and boosting dose) were administered 4 weeks apart. Blood was collected from the mandibular sinus immediately before and 2 weeks after the first immunization, immediately before the boosting dose, and at 2 and 4 weeks after the boosting dose.

Terminal splenectomies were performed on half (n=5) of all ten groups immediately before administration of the boosting dose and on the other half (n=5) following the final blood collection. The protocol for the animal studies was approved by the Institutional Animal Care and Use Committee at Cornell University (protocol number 2009-0096).

Assessing OMV Vaccine Immune Response.

Standard microtiter ELISA was performed on collected serum samples from vaccinated mice in 96-well plates. Wells were incubated with purified GFP overnight, followed by serial dilution incubation with serum. Secondary antibodies for IgG, IgM, IgG1, and IgG2 were subsequently incubated and detected using HRP. Hemagglutination inhibition assays were run using serum incubations with formalin-neutralized PR8 and X31 virus, and were detected via visual inspection of hemagglutination patterns. ELISA was also used to quantify antigen-specific T-cell response. Purified splenic T-cells were cultured for 7 days in complete RPMI, then seeded into wells and incubated in triplicate with GFP for 48 h. Anti-IFN-γ, IL-4, and IL-10 antibodies were then used to detect the presence of stimulated cytokine release. Further proliferation analysis on T-cells was also completed on similarly cultured T-cells. Cultured T-cells were trypsinized, centrifuged at 1000 rpm, and diluted to $1\times10^6$ cells/mL in complete RPMI, then labeled with CFSE (Invitrogen). $2\times10^5$ cells were seeded into 96-well plates, incubated with 30 μL 100 μg/mL GFP, and allowed to proliferate at 37° C. for 4 days. FACS was used to assess loss of CFSE in proliferating cells. Additional in vivo inflammation response analysis was done using subdermal injections in BALB/c mice ears (n=4), on which histopathology was conducted 30 h post-injection of the OMV samples.

In Vitro Analysis of Immune Cell Stimulation by EcN OMVs.

Bone marrow-derived macrophages were harvested from BALB/c femur bone marrow, column purified, and cultured in complete RPMI for 7 days. Following this, they were plated in 6-well plates, incubated with ClyA-GFP(+) OMVs, and assessed for phagocytosis-induced fluorescence and IL-12/4/10 expression via FACS analysis. T-cell activation via OMV-pulsed dendritic cells was assessed using DCs incubated for 2 days with OMVs; coculture was conducted with CFSE-labeled T-cells in 24-well plates and proliferative analysis was done 7 days following initial seeding. CFSE-labeled B-cells were assessed identically to antigen-restimulated T-cells, as described previously.

Statistical Analyses.

Statistical significance was determined by unpaired two-tailed Student's t-test or by ANOVA grouped test with supplemental Tukey's HSD tests when appropriate. Significance was determined to be at a confidence interval of $P<0.05$. Proteomic data was cross-referenced between three E. coli proteome libraries to determine identifications at $P<0.001$.

Figure 5:
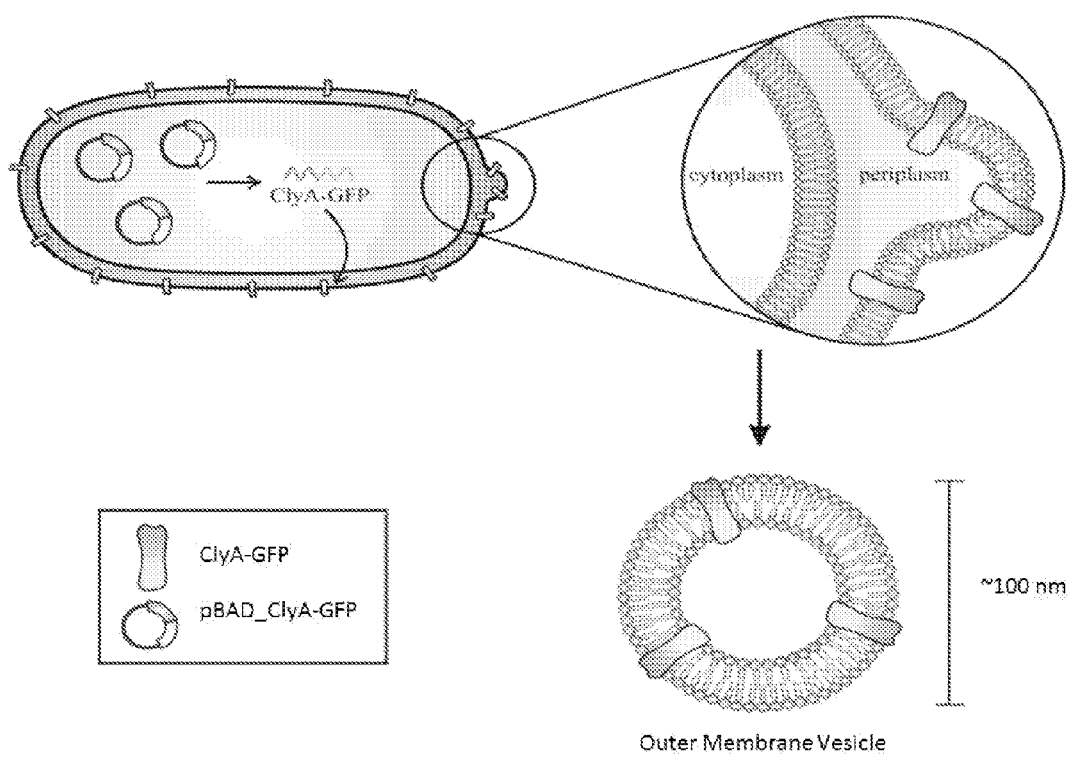
FIG. 5 illustrates generating engineered, custom antigen-presenting OMVs from *E. coli*. *E. coli* genetically modified to overproduce OMVs (such as via nlpI mutation used herein) are transformed with a plasmid encoding the appropriate ClyA-antigen fusion, in this case ClyA-GFP. Once transcribed, ClyA co-localizes the chimera to the *E. coli* outer membrane. As the bacteria continuously bud off OMVs, and the plasmids are designed to be under a high-copy-number promoter, the average OMV generated through the induced hypervesiculation will have a substantial number of recombinant ClyA-antigen fusions included in its membrane.

Example 1—EcN OMVs are Engineered as Recombinant Antigen Carriers Via a ClyA-Fusion Mechanism Previously, the successful expression and functional folding of a variety of recombinant antigens on the surface of K12 E. coli OMVs by inducing expression of a chimera consisting of the antigen fused to the C-terminus of enterobacterial cytotoxin ClyA was reported (Kim et al., "Engineered Bacterial Outer Membrane Vesicles with Enhanced Functionality," J. Mol. Biol. 380: 51-66 (2008), which is hereby incorporated by reference in its entirety) (FIG. 5).

Figure 6:
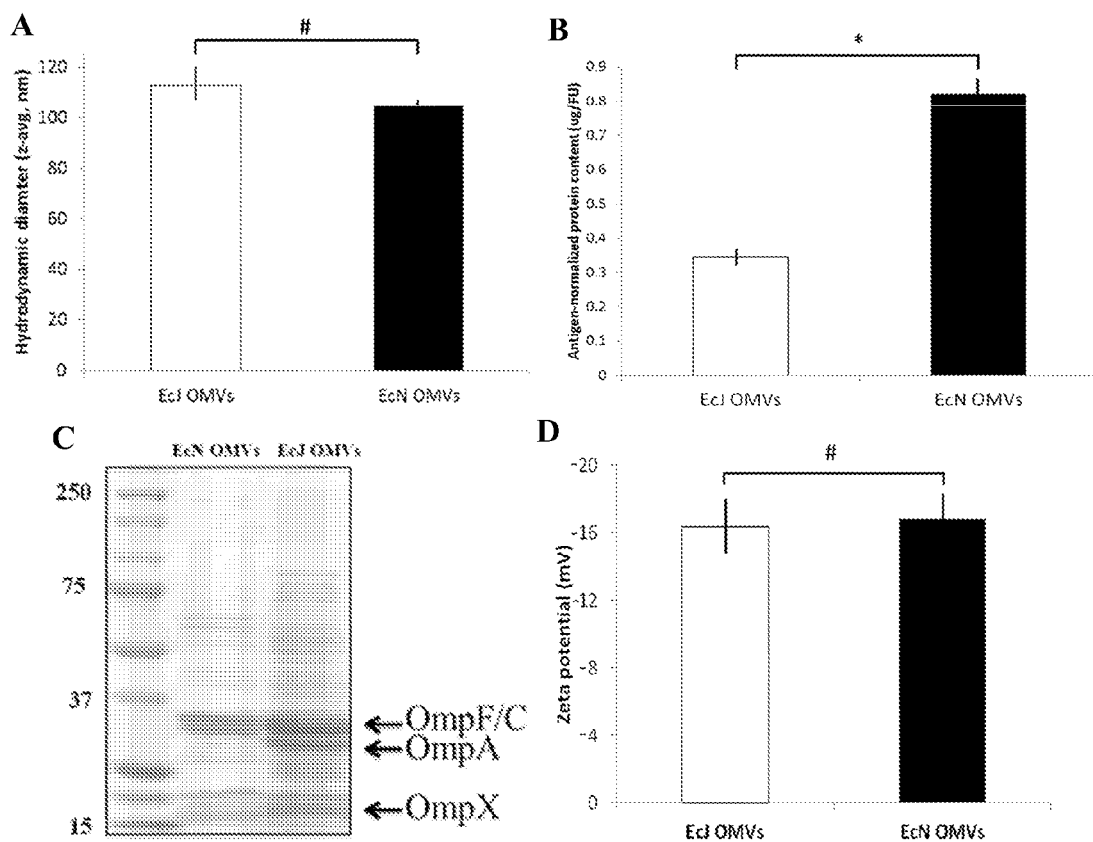
FIG. 6A-6D shows further comparative analysis of EcN and EcJ OMV vaccine formulations.

For the present study, green fluorescent protein (GFP) was selected as the primary model antigen for two reasons. First, GFP's natural fluorescence allowed simple quantitation of antigen content in all vaccine preparations, owing to the ClyA-antigen chimera's capacity to retain proper antigen folding upon outer membrane insertion (Chen et al., "Delivery of Foreign Antigens by Engineered Outer Membrane Vesicle Vaccines," Proc. Nat. Acad. Sci. USA 107:3099-3104 (2010), which is hereby incorporated by reference in its entirety). GFP's second advantage was its poor immunogenicity in mice, which allowed for maximal demonstration of the vaccine carrier's immunostimulatory potential. OMV overproduction was induced in EcN via genetic knockout of nlpI (Kim et al., "Engineered Bacterial Outer Membrane Vesicles with Enhanced Functionality," J. Mol. Biol. 380: 51-66 (2008); McBroom and Kuehn, "Release of Outer Membrane Vesicles by Gram-Negative Bacteria is a Novel Envelope Stress Response," Mol. Microbiol. 63:545-558 (2007), which is hereby incorporated by reference in its entirety) to produce the antigen delivery platform (FIG. 1A). OMVs released by the hypervesiculating EcN mutants expressing ClyA-GFP exhibited uniform size and shape while retaining characteristic bilipid membrane structure (FIG. 1B) and carried fluorescent membrane-bound GFP (FIG. 1C). To demonstrate the effect of probiotic strain-selection on the immune response, similar GFP-containing OMVs were produced as a control using non-probiotic K12 E. coli strain JC8031 (EcJ) (Kim et al., "Engineered Bacterial Outer Membrane Vesicles with Enhanced Functionality," J. Mol. Biol. 380: 51-66 (2008); Chen et al., "Delivery of Foreign Antigens by Engineered Outer Membrane Vesicle Vaccines," Proc. Nat. Acad. Sci. USA 107:3099-3104 (2010), which is hereby incorporated by reference in its entirety). Western blot analysis confirmed comparable ClyA-GFP content in both OMV preparations (FIG. 1D), allowing for meaningful comparisons between the two strains' abilities to trigger an immune response against the model antigen. As the purpose of using EcN as a vaccine carrier source derives molecularly from a hypothesized PAMP-dependent advantage, discrepancies between EcJ and EcN OMV TLR-agonist composition (FIG. 1E) were investigated. Surprisingly, it was found that EcN and EcJ OMVs contained similar amounts of membrane-bound lipopolysaccharide (LPS), a known key contributor in OMV-induced immune responses (Ellis and Kuehn, "Virulence and Immunomodulatory Roles of bacterial Outer Membrane Vesicles," Microbiol. Mol. Biol. Rev. 74:81-94 (2010), which is hereby incorporated by reference in its entirety). However, while total protein content of both E. coli-derived OMVs appeared generally similar (FIG. 6), as expected, several major PAMP-rich TLR agonists were substantially enriched in EcN OMVs. This discrepancy could form the biomolecular basis of the hypothesized immune cell targeting and self-adjuvancy advantage that was desired to harness.

Figure 7:
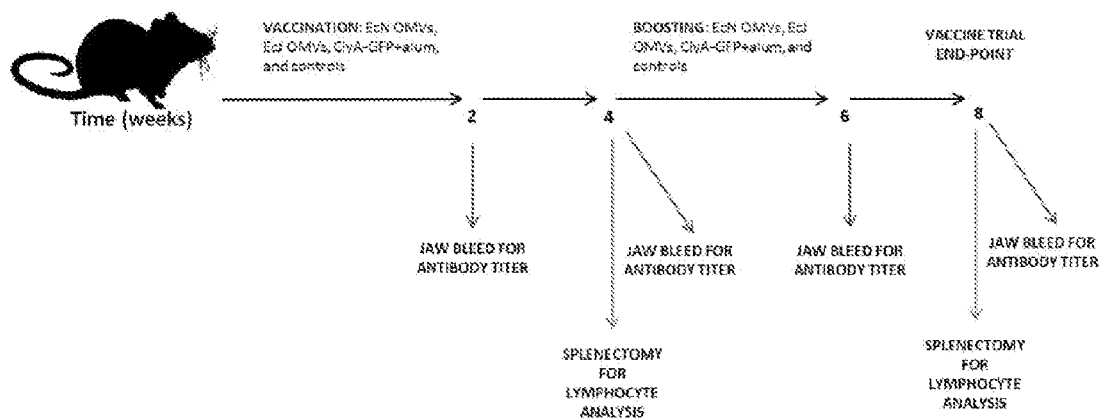
FIG. 7 shows a schematic of vaccination regimen for murine model immunization. At time of initial vaccination, n=10 mice were vaccinated; at t=4 wk, n=5 mice were sacrificed for splenectomy, leaving n=5 mice to continue the experiment to its conclusion at t=8 wk. t=0 wk is referred to as the "Pre prime" period, 0<t<4 wk is referred to as the "Post prime" period, t=4 wk is referred to as the "Pre boost" period, and 4<t≤8 wk is referred to as the "Post boost" period.
Figure 8:
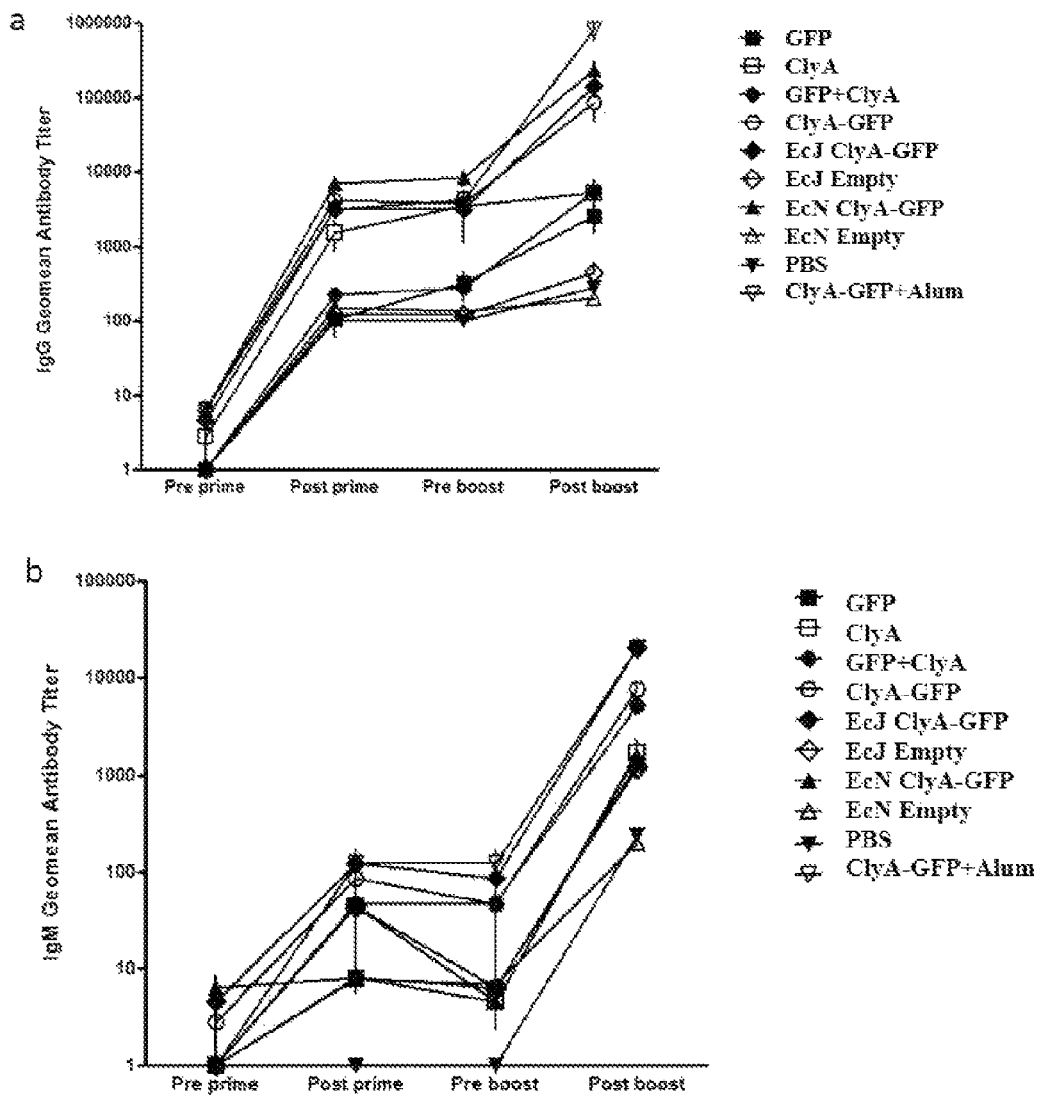
FIG. 8A-8B shows progressive generation of humoral immunity by EcN and EcJ OMV vaccines. Serum samples from jaw bleeds of all mice participating in the experiment were assayed for GFP-specific (FIG. 8A) IgG and (FIG. 8B) IgM at four time points: immediately prior to injection with priming vaccination dose (t=0 wk), following the priming vaccination (t=2 wk), immediately prior to injection with boosting vaccination dose (t=4 wk), and at the termination of the experiment (t=8 wk). Titers were determined by ELISA. All values are given as mean+/-s.d.
Figure 9:
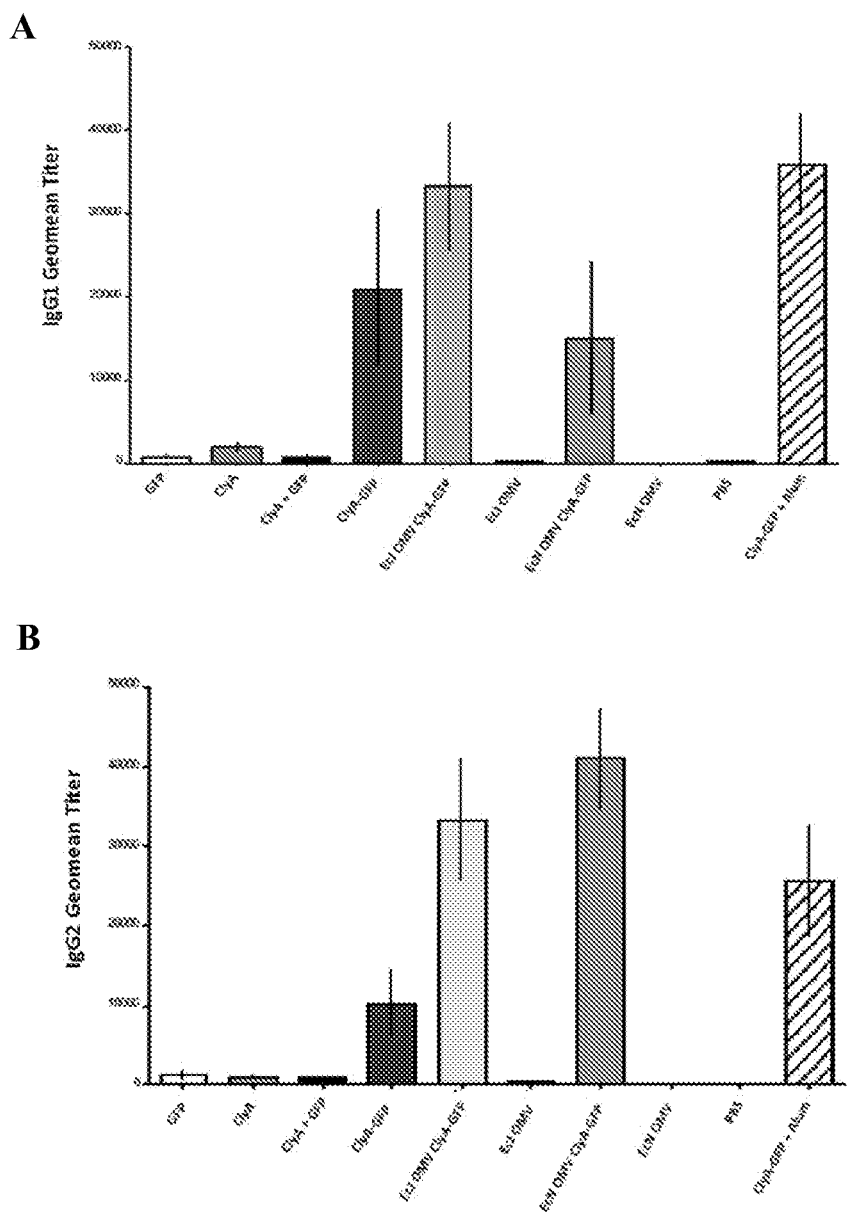
FIG. 9A-9B shows anti-GFP IgG1 and IgG2 serum titers from immunized and boosted mice. Serum samples from all mice (n=5) at the conclusion of experiment (t=8 wk) were assayed for anti-GFP (FIG. 9A) IgG1 and (FIG. 9B) IgG2 titers. Titers were determined by ELISA. All values are given as mean+/-s.d.

Example 2—Immunization with EcN OMVs Induces Antigen-Specific $T_H1$-Biased Immunity To test the ability of EcN OMVs to generate a strong adaptive response to GFP, BALB/c mice were immunized via subcutaneous injection with formulations of OMVs containing ClyA-GFP and free of additional adjuvant (FIG. 7). To ensure the presence of a substantially competitive positive control, vesicle-free ClyA-GFP adsorbed onto an enhanced aluminum hydroxide (alum) adjuvant delivery system, Alhydrogel® was separately injected. IgG titers assayed four weeks after the final boost indicated induction of a strong humoral response by both EcN and EcJ OMVs comparable to the gold standard of alum (FIG. 2A), consistent with previous work (Chen et al., "Delivery of Foreign Antigens by Engineered Outer Membrane Vesicle Vaccines," *Proc. Nat. Acad. Sci. USA* 107:3099-3104 (2010), which is hereby incorporated by reference in its entirety) and reflective of progressive generation of a robust response (FIG. 8). However, IgM titers showed some divergence in the humoral responses (FIG. 2B), with lower IgM levels generated by EcN OMVs indicating either early class-switching or a discrepancy in B-leukocyte stimulation by membranous endotoxins. Further divergence could be seen in IgG1 versus IgG2 titers. The EcN OMVs elicited an IgG2-dominant humoral response (FIG. 2C), which taken together with the relative decrease in final IgM titer suggests induction of a $T_H1$-facilitated immune response consistent with heightened cellular immunity stimulation (Mbulaiteye et al., "H. *Pylori*-Infection and Antibody Immune Response in a Rural Tanzanian Population," *Infect. Agent. Cancer* (2006), which is hereby incorporated by reference in its entirety). In contrast, EcJ OMVs mirrored the alum-positive control with a larger IgG1 fraction, suggesting a less remarkable response more in line with standard adjuvants. As a result, these data not only indicate that the EcN OMVs can function as an effective antigen carrier for stimulating humoral immunity, but additionally suggest a strain-dependent advantage conferred by EcN in stimulating a traditionally elusive $T_H1$ response.

Unfortunately, demonstration of high antigen-specific immunoglobulin titers, while useful in predicting a strong vaccine response, does not necessarily imply a functional humoral response. A better prediction of functional immunoglobulins involves probing for successful antibody opsonization/neutralization of a target antigen moiety. As the primary model antigen, GFP, could not facilitate such an analysis, codon-optimized H1N1 influenza hemagglutinin was secondarily expressed as a ClyA-antigen fusion to enable surface display on the EcN OMVs. The subcutaneous vaccinations of BALB/c mice were repeated and again compared the results to that of a ClyA-antigen Alhydrogel® mixture. In this specific case, the H1N1 influenza strain A/PR8/34 virus was used and assayed for hemagglutination inhibition. Serum from vaccinated mice successfully blocked hemagglutination of mouse red blood cells at comparable titers to the positive control of alum (FIG. 2D), demonstrating the desired retention of functional antibody generation. As there was additional interest in whether or not surface display of the HA antigen on the EcN OMV would lead to an expanded range of target epitopes (Chen et al., "Delivery of Foreign Antigens by Engineered Outer Membrane Vesicle Vaccines," *Proc. Nat. Acad. Sci. USA* 107: 3099-3104 (2010), which is hereby incorporated by reference in its entirety), the assay was also run against H3N2 influenza strain X31 virus to test for cross-reactivity. Interestingly, mouse serum from EcN OMV-vaccinated mice significantly outperformed that of the alum control mice (FIG. 2D), indicating not only sufficient presence of opsonizing/neutralizing antibody titers that support the generation of a protective humoral response, but titers capable of cross-strain protection as well.

Figure 2:
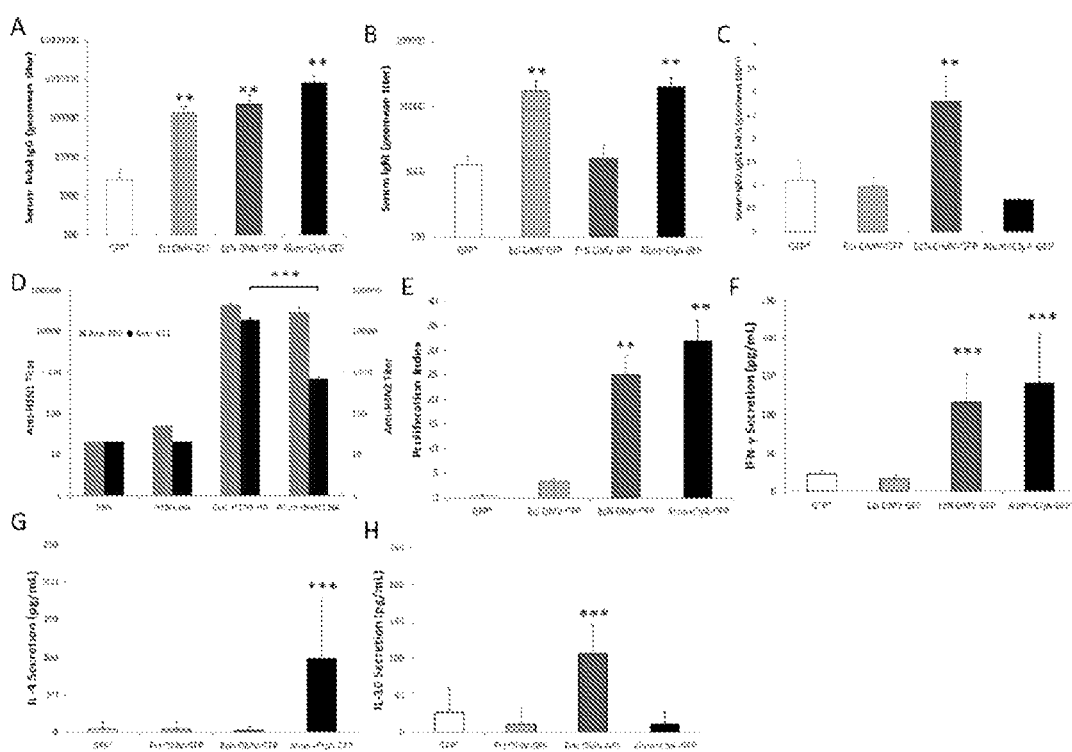
FIG. 2A-2H shows the EcN OMV platform generates robust humoral and cellular immune response in a mouse model.
Figure 10:
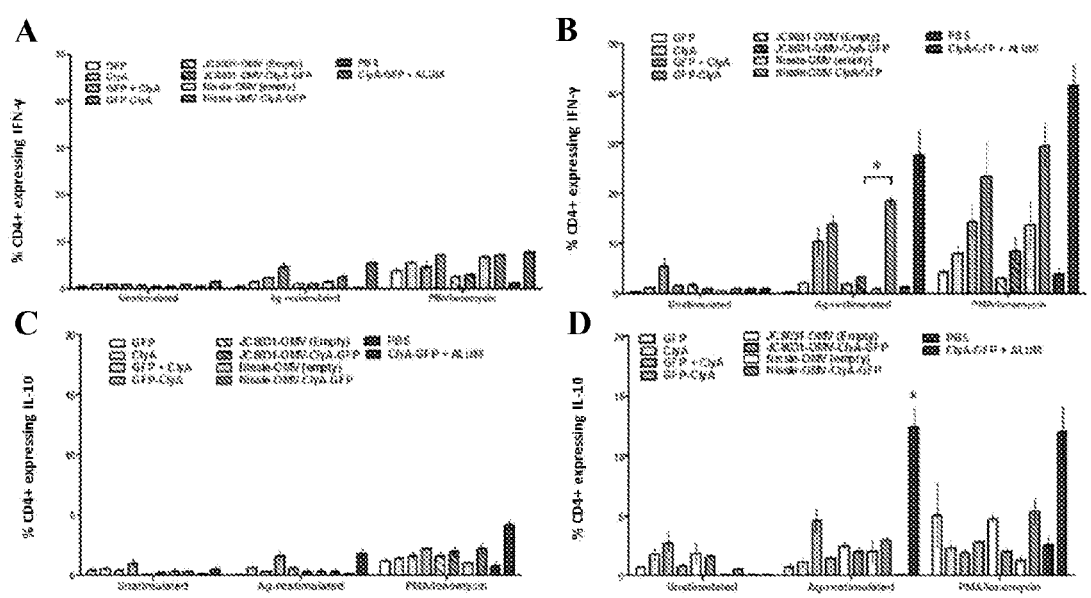
FIG. 10A-10D shows divergent induction of cytokine expression in spleen-derived, restimulated mouse T-cells by EcN and EcJ OMV vaccines indicates superior cellular immunity potential for EcN OMVs. Mouse spleens were harvested (n=5) pre-boost (t=4 wk.

Further analysis of the mice's OMV-induced adaptive immunity revealed a favorable T-cell response reflective of the EcN OMVs' divergent humoral response. Specifically, spleen-derived T-cells from mice vaccinated with ClyA-GFP EcN OMVs had proliferation responses to antigen restimulation comparable to the alum-positive ClyA-GFP control and significantly greater than that triggered by EcJ OMVs (FIG. 2E). This result is generally indicative of a superior immunostimulatory effect on naïve T-cell populations, and is in direct agreement with the driving hypothesis that the EcN membrane may be privileged as an adjuvant material in its ability to actively target T cells. Moreover, EcN but not EcJ OMVs promoted a similarly dramatic increase in antigen-restimulated T-cell IFN-γ secretion (FIG. 2F) and expression levels (FIGS. 10, A and B). Taken together, these results highlight the ability of EcN OMVs to induce a strong cellular immune response, which correlates well with the $T_H1$ response suggested by the IgG2:IgG1 ratio. Depressed IL-4 (FIG. 2G) and IL-10 (FIG. 2H, FIGS. 10, C and D) levels relative to IFN-γ further support the induction of a favorable $T_H1$-biased response by EcN OMVs. To date, this level of $T_H1$-indicative IFN-γ/IL-4 discrepancy has rarely been reported in the literature for adjuvant-free subunuit vaccine carriers, and never for OMV-based systems. Importantly, this also sets it aside from standard adjuvants such as alum, which produce a mixed $T_H1/T_H2$ response that is often insufficient at leveraging the advantage of $T_H1$ immunity against certain intracellular pathogens. Also of note was the observation that IL-10 secretory activity from EcN OMV restimulation was elevated relative to EcJ OMVs and the alum-positive control. Considering the successful induction of elevated T-cell IFN-γ levels, this suggests a unique use of IL-10 in a supplementary and indirectly beneficial role in generating a favorable yet non-detrimental T-cell response, such as influencing a shift in the $T_H1/T_H2$ balance while controlling potential runaway inflammation (Klier et al., "Immunostimulation of Bronchoalveolar Lavage Cells From Recurrent Airway Obstruction-Affected Horses by Different CpG-Classes Bound to Gelatin Nanoparticles," *Vet. Immunol. Immunopathol.* 147:79-87 (2011), which is hereby incorporated by reference in its entirety). Taken together, the antigen-specific humoral and cellular immunity induced by the EcN OMV carriers are indicative both of a protective vaccine response (Weeratna et al., "CpG DNA Induces Stronger Immune Responses With Less Toxicity Than Other Adjuvants," *Vaccine* 18: 1755-1762 (2000), which is hereby incorporated by reference in its entirety) and, more importantly, a response tuned to be useful in targeting pathogens that are most effectively neutralized by the more elusive $T_H1$-biased response (Mosmann et al., "TH1 and TH2 Cells: Different Patterns of Lymphokine Secretion Lead to Different Functional Properties," *Annu. Rev. Immunol.* 7: 145-173 (1989), which is hereby incorporated by reference in its entirety).

Example 3—EcN OMVs Strongly Engage LPS-Dependent/Independent Innate Immunity

Figure 3:
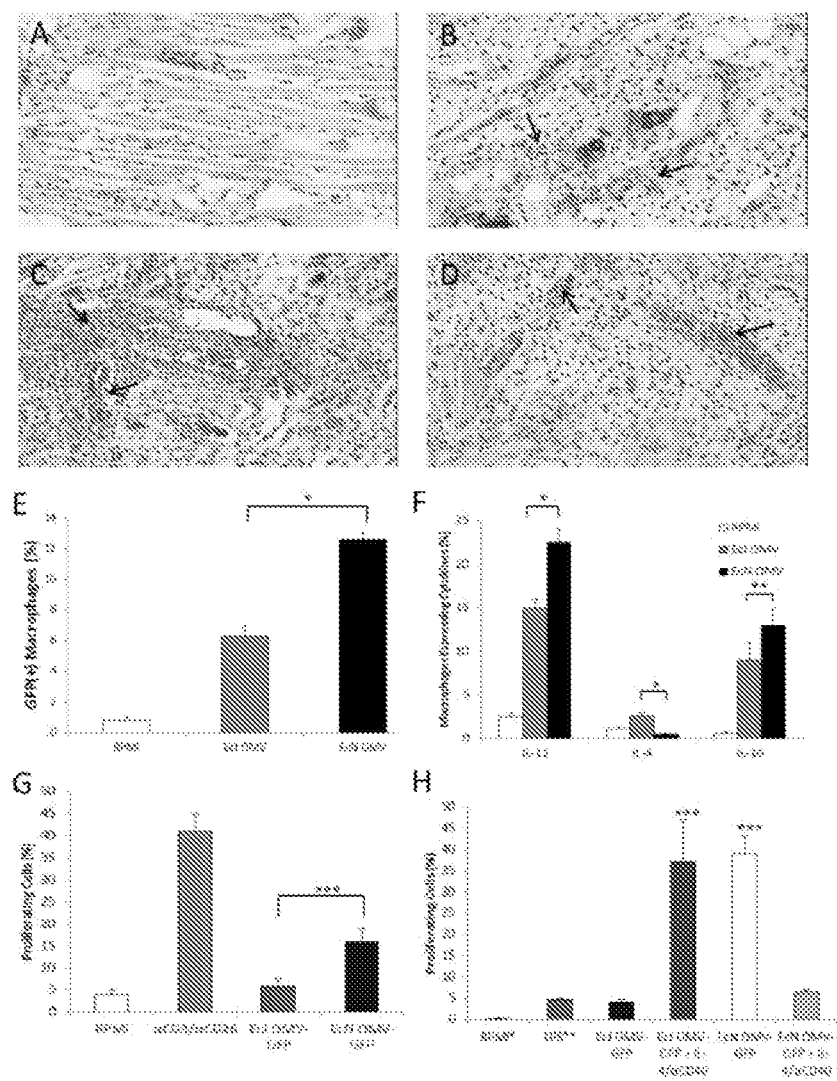
FIG. 3A-3H shows EcN OMVs effectively stimulate robust innate and adaptive immunity.
Figure 4:
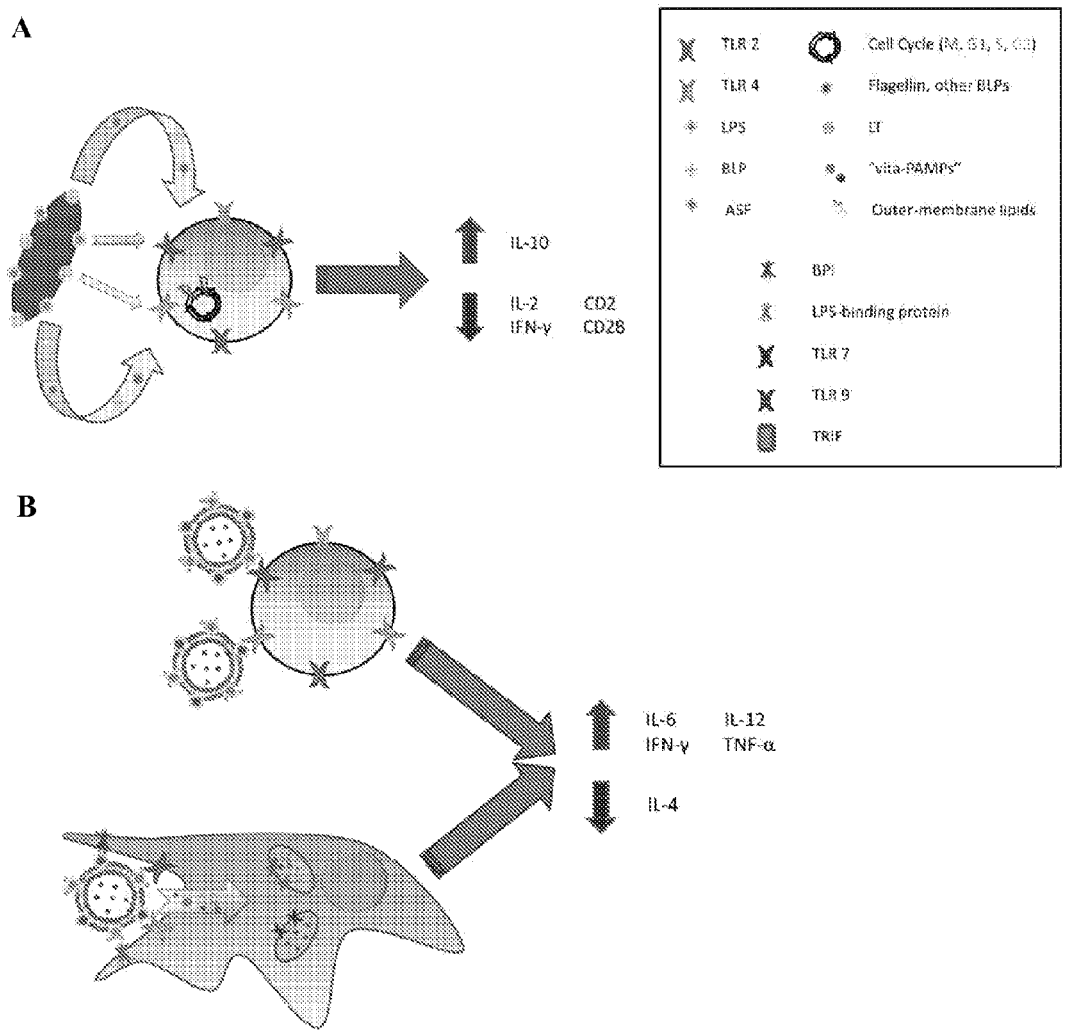
FIG. 4A-4B shows isolation of EcN immunostimulatory factors from immunosuppressive ones via OMV formation leads to an induction of a strong immune response.
Figure 11:
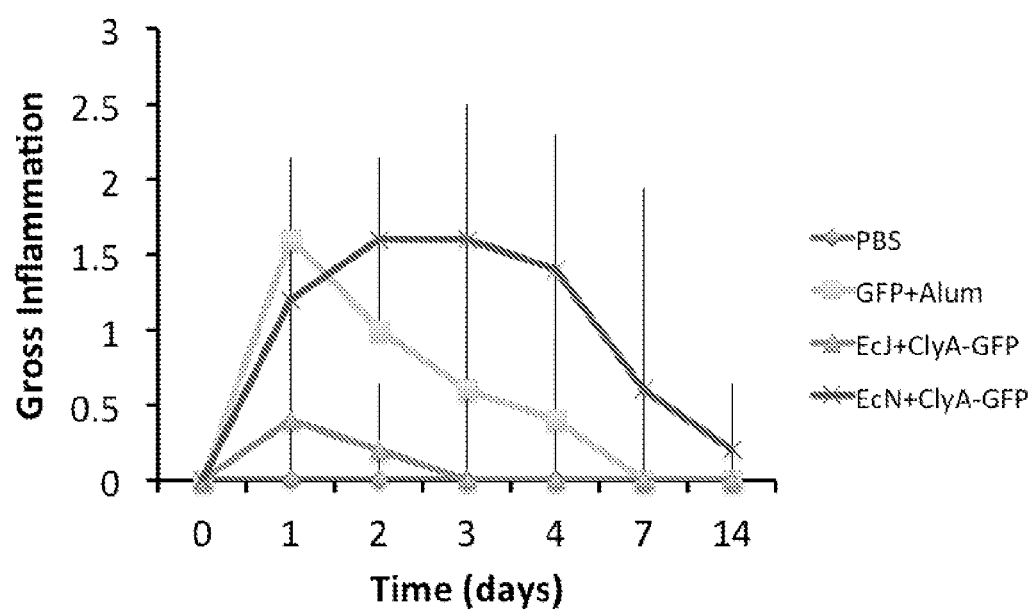
FIG. 11 shows inflammation in vaccinated mice is similar between adjuvancy sources Alhydrogel®, EcJ OMVs, and EcN OMVS. Gross inflammation (n=5) was graded 0-3, with 0 being equal to no apparent inflammation, 1 being mild redness causing no visible irritation, 2 being moderate redness causing no visible irritation, and 3 being moderate-to-severe redness resulting in substantial dryness and scabbing as well as evident irritation. All values are given as mean+/-s.d.

A key determining factor in adaptive immune response generation is the extent to which innate immunity is engaged (Schijns et al., "Vaccine Immunopotentiators of the Future," *Clin. Pharmacol. Ther.* 82:750-755 (2007), which is hereby incorporated by reference in its entirety). While on a macroscopic level OMV vaccine inflammation was observed to be similar to that of the alum control in duration and recovery time (FIG. 11), such observations are not necessarily reflective of an adjuvant's capacity for local immune cell engagement and recruitment. Hence, the capacity of EcN OMV self-adjuvancy to robustly induce an innate response via initial dermal inflammation was further explored. Using a subdermal injection model in a BALB/c mouse ear and subsequent histological analysis, the acute inflammation response generated by both EcN and EcJ OMVs was assessed. The resulting inflammopathology revealed a surprisingly marked difference. At 30 h post-injection, EcN OMVs demonstrated the ability to dramatically remodel the dermal tissue, cause local vasculature swelling, and recruit dense populations of leukocytes (FIG. 3C) relative to a blank PBS control (FIG. 3A). Such a reaction is an established sign of an adjuvanting material capable of stimulating the required innate immunity activation for a good vaccine response (Schijns et al., "Vaccine Immunopotentiators of the Future," *Clin. Pharmacol. Ther.* 82:750-755 (2007) and Calabro et al., "Vaccine Adjuvants Alum and MF59 Induce Rapid Recruitment of Neutrophils and Monocytes That Participate in Antigen Transport to Draining Lymph Nodes," *Vaccine* 29:1812-1823 (2011), which are hereby incorporated by reference in their entirety). EcJ OMVs, on the other hand, stimulated a much less dramatic inflammatory response with an equivalent OMV dosage (FIG. 3B). Taken together, these data imply that the probiotic strain-dependent nature of EcN OMVs' unique immune response is in part dependent on a strong stimulation of innate immunity.

Figure 12:
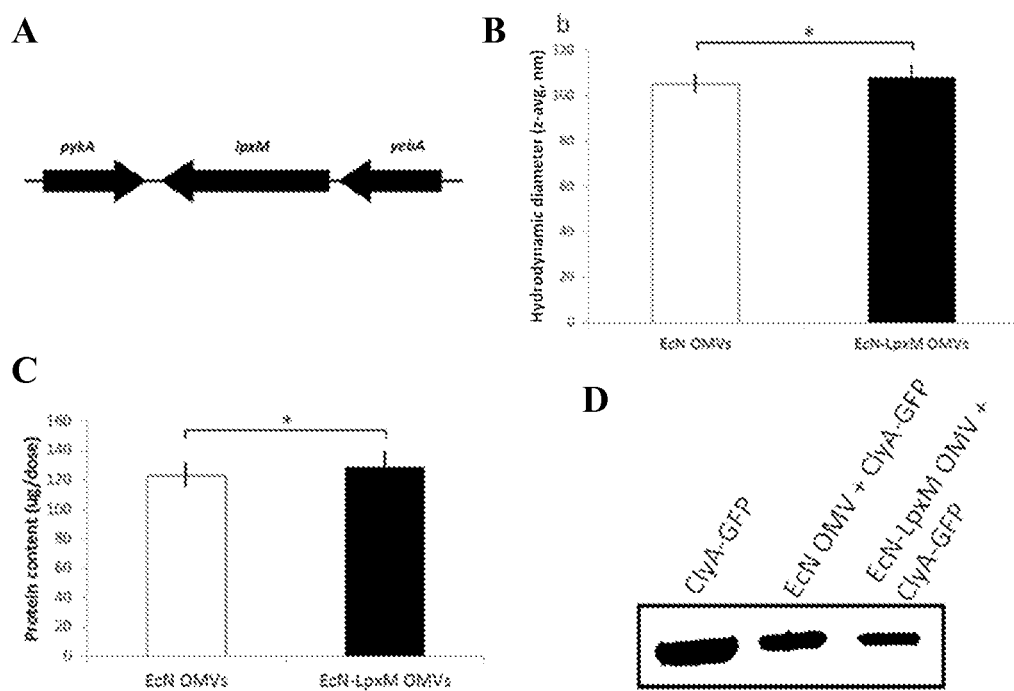
FIG. 12A-12D shows LpxM-mutant EcN OMV generation does not appreciably alter OMVs.
Figure 13:
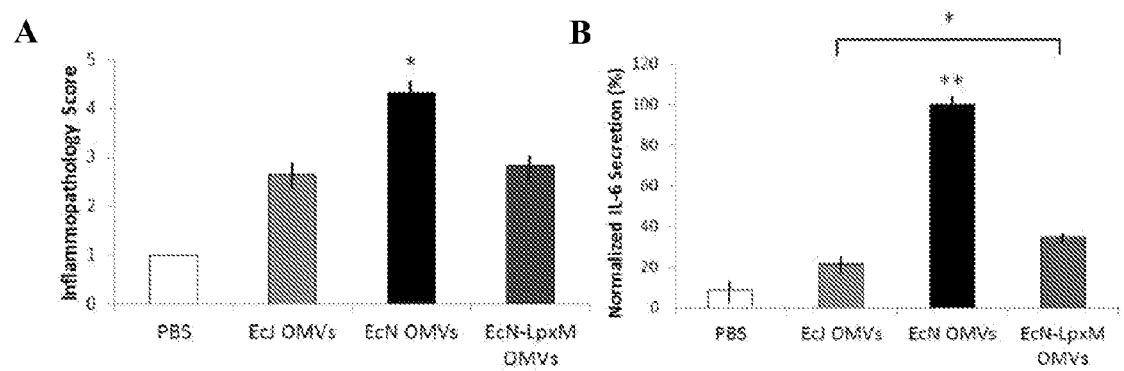
FIG. 13A-13B shows LpxM mutation confers quantifiable reduction, but not ablation, of proinflammatory OMV response.

Importantly, the strain-variable innate immune stimulation resulted from equivalent doses of OMV-bound LPS, generally considered to be the most important innate bacterial immunomodulator (Ellis et al., "Virulence and Immunomodulatory Roles of Bacterial Outer Membrane Vesicles," *Microbiol. Mol. Biol. Rev.* 74:81-94 (2010), which is hereby incorporated by reference in its entirety). This result implies that the immunostimulatory mechanism for the EcN OMVs is not fully dependent on the fairly toxic bacterial moiety. Therefore, it was next investigated whether or not direct reduction of LPS-induced endotoxicity would substantially attenuate the enhanced innate response observed with EcN OMVs. A genetic knockout of the lpxM gene in *E. coli* inactivates the MsbB lipid A acyltransferase and is known to minimize LPS-based endotoxicity (Kim et al., "Structural Modifications of Outer Membrane Vesicles to Refine Them as Vaccine Delivery Vehicles," *Biochim. Biophys. Acta.* 1788:2150-2159 (2009), which is hereby incorporated by reference in its entirety); therefore, lpxM was knocked out in the EcN nlpI mutant to generate mutant EcN OMVs (FIG. 12) and allow investigation of the influence of LPS on the activation of the innate response. Following identical subdermal mouse ear injections, the previously observed inflammopathology was partially attenuated but ultimately still reflective of an appreciable inflammatory response (FIG. 3D and FIG. 13). Thus, a non-endotoxicity-dependent, probiotic strain-dependent advantage in innate immunity stimulation is conferred by EcN as an OMV source, possibly due to the presence of other highly active immunostimulatory membranous PAMPs (Ellis et al., "Naturally Produced Outer Membrane Vesicles from *Pseudomonas aeruginosa* Elicit a Potent Innate Immune Response via Combined Sensing of Both Lipopolysaccharide and Protein Components," *Infect. Immun.* 78:3822-3831 (2010), which is hereby incorporated by reference in its entirety) and TLR agonists as suggested by the proteomic analysis discussed above.

Figure 14:
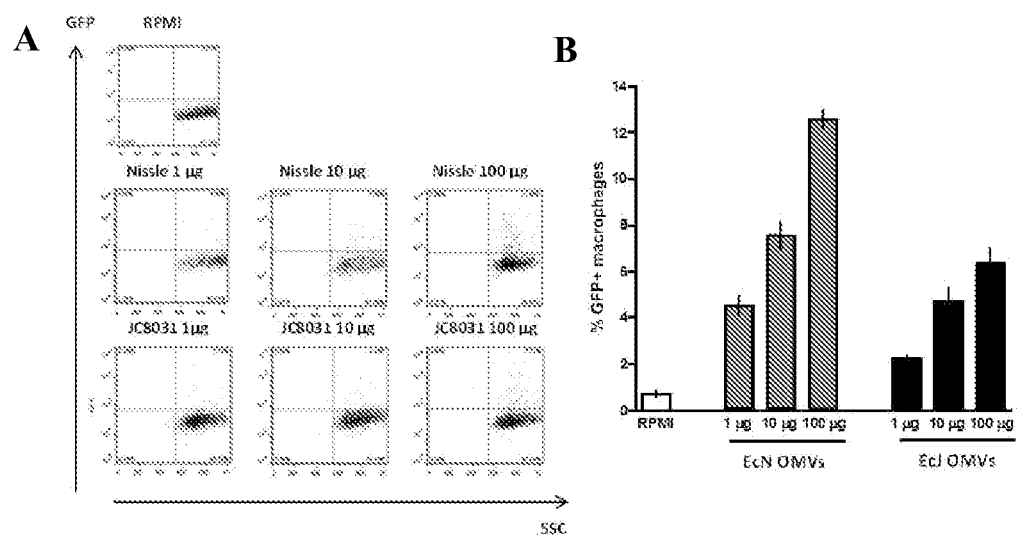
FIG. 14A-14B shows EcN OMVs stimulate stronger phagocytic responses in macrophages. Primary macrophages cultured from BALB/c mouse bone marrow were incubated with variable quantities of ClyA-GFP(+) EcN or EcJ OMVs and assayed for fluorescence levels via FACS.
Figure 15:
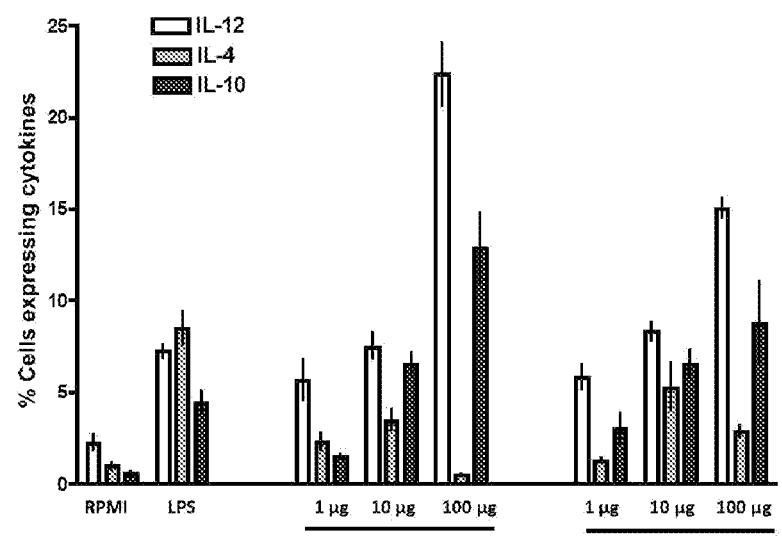
FIG. 15 shows EcN and EcJ OMVs induce divergent macrophage cytokine expression post-incubation. Primary macrophages cultured from BALB/c mouse bone marrow were incubated with variable quantities of ClyA-GFP(+) EcN or EcJ OMVs, tagged for cytokine expression, and analyzed via FACS. Masses given represent amount of OMVs added as determined by total protein content. All values are given as mean+/−s.d.

Analysis of EcN OMV macrophage stimulation, an important cellular component of innate immunity, provided additional support for an enhanced probiotic strain-dependent mechanism of innate immunity stimulation. When bone marrow-derived mouse macrophages (BMMs) were incubated with equivalent amounts of ClyA-GFP-containing EcN and EcJ OMVs, they internalized a significantly greater number of the former (FIG. 3E and FIG. 14). These results suggest that the EcN outer membrane is a more potent activator of macrophage phagocytosis. Further analysis of BMM cytokine expression profiles following OMV incubation additionally revealed a significant discrepancy in IL-12 and IL-4 expression induced by EcN and EcJ OMVs (FIG. 3F and FIG. 15). Specifically, EcN OMVs stimulated elevated IL-12 but not IL-4 expression relative to EcJ OMVs, indicating a propensity for EcN OMVs to facilitate $T_H1$ dominance during the adaptive immunity transition. This may highlight a synergistic coupling of enhanced targeting via superior PAMP-dependent TLR crosslinking and subsequent intracellular delivery of membranous and soluble bacterial factors (Ellis et al., "Virulence and Immunomodulatory Roles of Bacterial Outer Membrane Vesicles," *Microbiol. Mol. Biol. Rev.* 74:81-94 (2010), which is hereby incorporated by reference in its entirety). The opposite expression levels induced by EcJ OMVs in turn suggests facilitation of a mechanism more in line with $T_H2$ bias (Hsieh et al., "Development of TH1 CD4+ T Cells Through IL-12 Produced by *Listeria*-Induced Macrophages," *Science* 260:547-549 (1993), which is hereby incorporated by reference in its entirety). These results corroborate previous observations of a $T_H1$-$T_H2$ discrepancy being crucial to the mechanistic benefits conferred by using the EcN OMVs.

Figure 16:
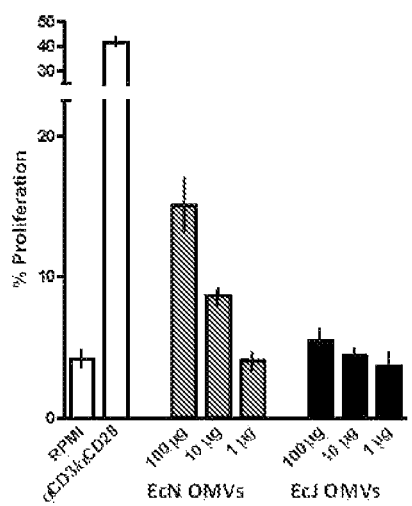
FIG. 16 shows naïve T-cells activated by OMV-primed dendritic cells demonstrate increased proliferation when stimulated with EcN OMVs. Primary bone marrow-derived BALB/c mouse dendritic cells were incubated with variable quantities of EcN or EcJ OMVs, then co-cultured with primary spleen-derived BALB/c mouse T-cells. T-cells were CFSE stained and analyzed via FACS. Masses given represent amount of OMVs added as determined by total protein content. All values are given as mean+/−s.d.

Example 4—Adaptive Immunity Stimulation is Facilitated by APC Targeting and $T_H1$-Biased Activation An important link between a heightened inflammatory response and the development of a strong adaptive T-cell response are antigen-loaded dendritic cells (DCs) that migrate from the site of inflammation to local lymph nodes (Bevan, M. J., "Understand Memory, Design Better Vaccines," *Nat. Immunol.* 12:463-465 (2011), which is hereby incorporated by reference in its entirety). To determine if DC-dependent T-cell activation could benefit from the strain-dependent immunomodulation induced by EcN OMVs, the ability of bone marrow-derived mouse DCs (BMDCs) incubated with EcN and EcJ OMVs to induce proliferation in spleen-derived mouse T-cells was assessed. The pronounced increase in naïve T-cell activation by BMDCs primed with EcN OMVs (FIG. 3G and FIG. 16) relative to those primed with EcJ OMVs suggests that the selection of EcN as the OMV source improved the ability of the OMVs to effectively interface with and stimulate antigen-presenting cells (APCs). Additionally, the ability of the EcJ OMV control to also stimulate T-cells through BMDC-dependent activation, albeit to a lesser extent than EcN OMVs, helps rule out the possibility that they caused a DC-dependent T-cell suppression (Trebichaysky et al., "Modulation of Natural Immunity in the Gut by *Escherichia coli* Strain Nissle 1917," *Nutr. Rev.* 68:459-464 (2010), which is hereby incorporated by reference in its entirety), which would have made conclusions concerning a strain-dependent $T_H1/T_H2$-bias discrepancy difficult.

Figure 17:
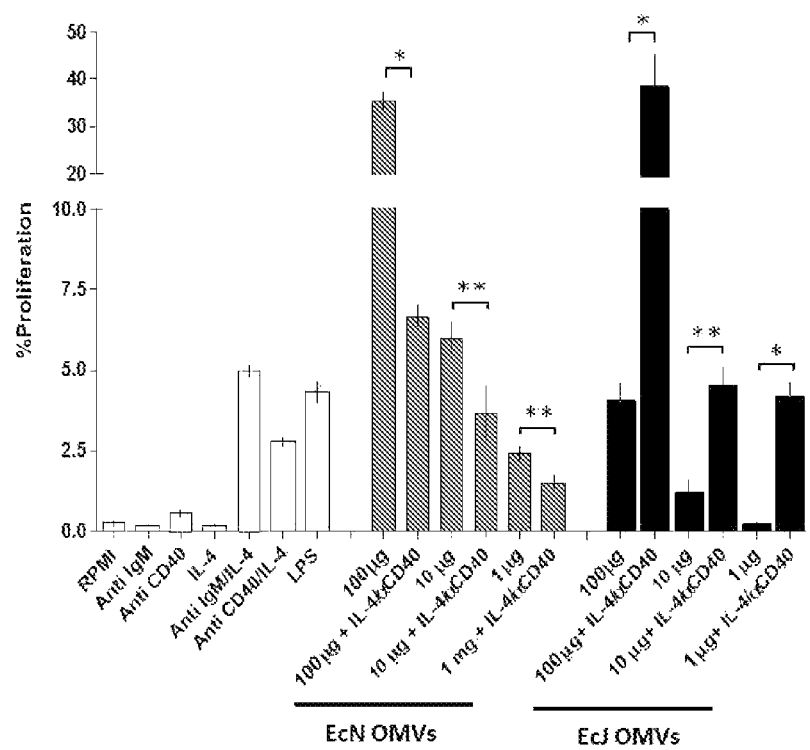
FIG. 17 shows B-cells are activated by EcN or EcJ OMVs via different mechanisms. Primary bone marrow-derived BALB/c mouse B-cells were incubated with various quantities of EcN or EcJ OMVs either in the presence or absence of T-cell-derived proliferation induction helper factors IL-4 and anti-CD40. *P<0.001, **P<0.01 as determined by Tukey's HSD post-hoc test. Masses given represent amount of OMVs added as determined by total protein content. All values are given as mean+/−s.d.

Taken together, the enhanced stimulation of both macrophages and DCs by EcN OMVs builds a strong case for a PAMP-dependent mechanism for enhanced activation of professional APCs as a crucial component of the robust induction of adaptive immunity to a recombinant antigen. These data led us to consider that the EcN OMVs' immunomodulatory capability might take advantage of similarly improved interactions with the third major APC, namely B-cells. A capacity for direct B-cell stimulation, and thus direct surface-displayed antigen presentation, would also help explain the enhanced cross-strain protection observed when H1N1 HA was used as the model antigen. Accordingly, induced proliferation of splenic mouse B-cells via incubation with EcN and EcJ OMVs was measured. This analysis revealed that EcN OMVs possessed significant potential for T-cell independent B-cell activation due to their ability to stimulate B-cell proliferation in the absence of T-cell helper factors (FIG. 3H and FIG. 17). Such activation is not uncommon in pathogen infection (Vos et al., "B-cell Activation by T-Cell-Independent Type 2 Antigens as an Integral Part of the Humoral Immune Response to Pathogenic Microorganisms," *Immunol. Rev.* 176: 154-170 (2000), which is hereby incorporated by reference in its entirety) and likely resulted from a combination of the presence of EcN PAMPs and OMV nanoscale avidity enhancement (Singh et al., "Nanoparticles and Microparticles as Vaccine-Delivery Systems," *Expert Rev. Vaccines.* 6:797-808 (2007), which is hereby incorporated by reference in its entirety). Interestingly, this phenomenon was in strong contrast to the EcJ OMV control's ability to activate B-cells, which was entirely dependent on the addition of T-cell helper factors IL-4 and anti-CD40. Such a strong discrepancy further highlights the important benefit EcN provides to *E. coli* OMV antigen carriers, providing robust humoral immunity through a supplemental T-cell independent mechanism that can work in parallel to, and perhaps even uniquely enhance, the establishment of a $T_H1$-biased adaptive response.

Example 5—Johne's Disease Vaccine

One of the great frontiers of current vaccine research is designing vaccines against complicated intracellular pathogens that the mammalian immune system normally has great difficulty clearing. Some pathogens, like the *Plasmodium* family of protozoan parasites, use intracellular evasion to dodge the immune system for fairly short amounts of time as they go through their life cycle within a mammalian host and cause great, often fatal, destruction in resident tissues (Girard et al., "A Review of Human Vaccine Research and Development: Malaria," *Vaccine* 25:1567-80 (2007), which is hereby incorporated by reference in its entirety). Others, like the *Mycobacterium* family (best known for causing tuberculosis in humans), use intracellular evasion inside macrophages themselves to lie dormant for decades before re-emerging as pathogenic (Baldwin et al., "The Importance of Adjuvant Formulation in the Development of a Tuberculosis Vaccine," *Journal of Immunology* 188:2189-97 (2012); Noss et al., "Toll-Like Receptor 2-Dependent Inhibition of Macrophage Class II MHC Expression and Antigen Processing by 19-kDa Lipoprotein of *Mycobacterium tuberculosis*," *The Journal of Immunology* 167:910-8 (2001); and Chen et al., "Immune Responses in Mice to *Mycobacterium avium* subsp. Paratuberculosis Following Vaccination with a Novel 74F Recombinant Polyprotein," *Vaccine* 26:1253-62 (2008), which are hereby incorporated by reference in their entirety). Regardless of the timescale of infection, intracellular evasion is best combatted by a $T_H1$-biased immune response, and it has been theorized that a leading factor in the consistent failure of vaccines against pathogens such as *Plasmodium* and *Mycobacterium* is a lack of sufficient antigen-specific $T_H1$ immunity induction. Therefore, it was hypothesized that the EcN OMV platform may be an ideal candidate for vaccines against such non-viral intracellular pathogens.

As the preliminary model pathogen to test this application, *Mycobacterium avium* subs. *paratuberculosis* (MAP), which causes Johne's disease in cattle was chosen (Chen et al., "Immune Responses in Mice to *Mycobacterium avium* subsp. Paratuberculosis Following Vaccination with a Novel 74F Recombinant Polyprotein," *Vaccine* 26:1253-62 (2008), which is hereby incorporated by reference in its entirety). Johne's disease is essentially the bovine analogue of human tuberculosis (TB), thus making it a compelling and highly relevant animal model to study given the billions of people currently infected globally with TB and the millions of new chronic active cases occurring each year. Basic anti-antigen immune response in BALB/c mice was tested. For the antigen of choice, however, a slightly different approach was taken. Instead of simply choosing a native antigen of MAP (as with H1N1 HA), the test of the platform's recombinant subunit antigen carrier applicability was broadened and the fusion polyprotein antigen MAP 74F (Chen et al., "Immune Responses in Mice to *Mycobacterium avium* subsp. Paratuberculosis Following Vaccination with a Novel 74F Recombinant Polyprotein," *Vaccine* 26:1253-62 (2008), which is hereby incorporated by reference in its entirety) was used. 74F contains a segmented fusion of MAP3527 and MAP1519, and its inclusion in this study represents an attempt to demonstrate that the ClyA-antigen expression pathway can be used to enhance vaccine antigen multivalency through multiple-antigen inclusion. Secondly, its choice pushes the boundaries of ClyA's ability to externalize a C-terminally fused moiety-74F is 803 amino acids long, substantially larger than the original model antigen GFP's 242 amino acids. It is highly likely that there is some upper limit to ClyA's ability to act as an externalizing transporter; a larger polyprotein such as 74F may serve as a useful probing of the upper limit.

Figure 18:
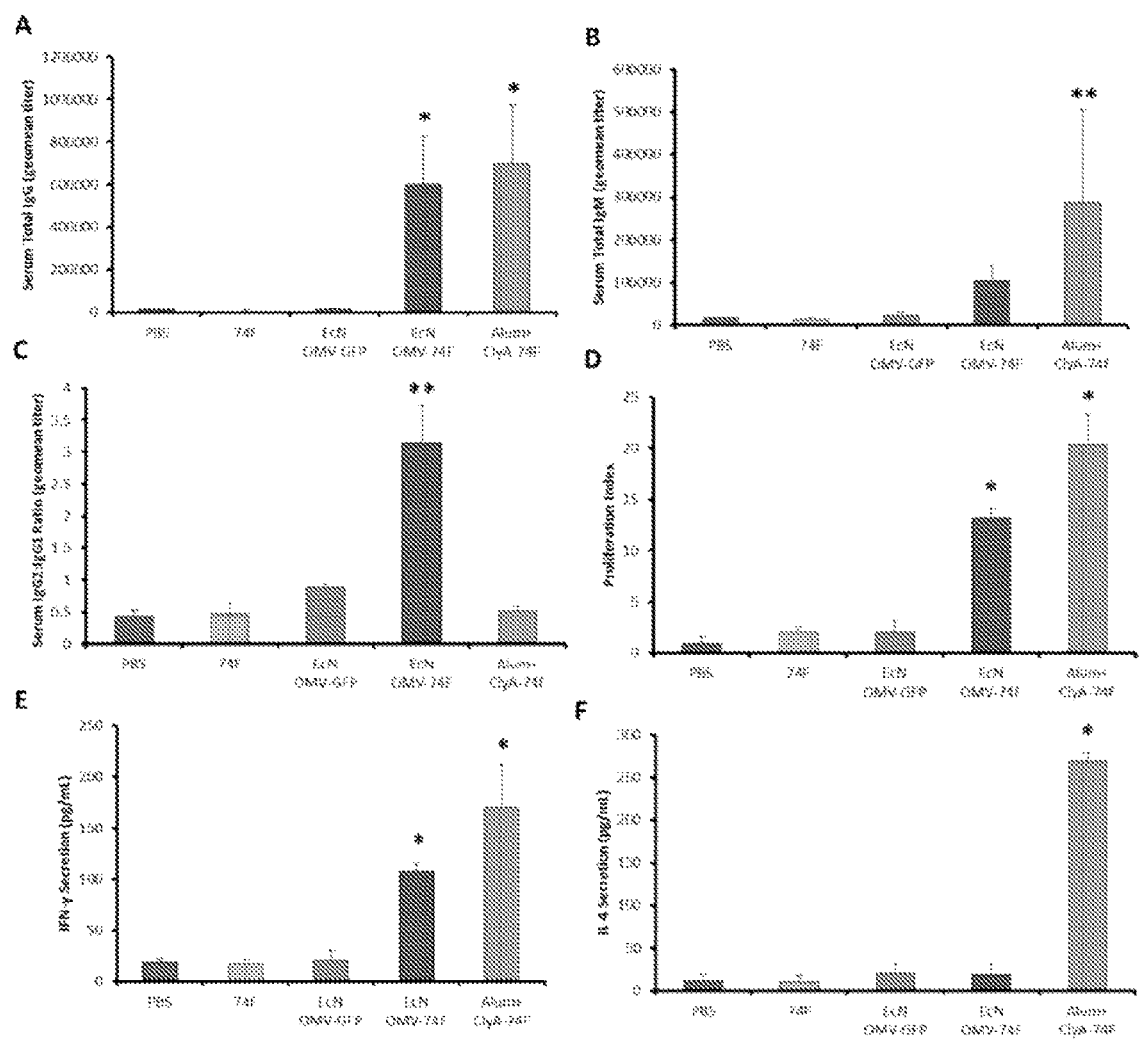
FIGS. 18A-F show EcN OMV carriers generate strong anti-MAP 74F humoral and cellular immunity. Terminal data points from BALB/c mice vaccinated and boosted once with antigen-normalized (or protein normalized, as appropriate) with EcN OMVs and controls (n=5).

The initial immunological data from that trial is promising. The humoral (FIG. 18A-18C) and cellular (FIG. 18D-18F) data clearly indicate that despite the larger size and complexity of the 74F polyprotein antigen, the EcN OMV was still able to deliver it as an antigen and facilitate the development of antigen-specific immunity. Of note is that there was indeed a slightly diminished response relative to alum that was not seen using H1N1 HA. At this stage, it is hard to determine whether that was the result of the nature of the 74F antigen itself, a diminished capacity of the EcN mutants to surface display the antigen via ClyA due to its size or some other antigen-related factor, or whether some additional factor of the trial itself played a role. Perhaps, most importantly, the data still indicates a strong enough response to the 74F antigen to be worth further investigation in a relevant animal challenge model, though future EcN OMV applications involving even larger antigens may require additional attention nonetheless.

Example 6—Peanut Allergy Vaccine

While pathogen vaccine targets are certainly the most obvious application of a recombinant subunit antigen carrier platform such as the EcN OMV, they are not the only ones. Indeed, setting aside the classic medical definition of a vaccine as a prophylactic immunological treatment of pathogenic organism infection, at its core a vaccine delivery platform is much more simply a targeted immunomodulator. That is, its purpose is to alter the immune response in a favorable way to an exogenous moiety of interest. This consideration has certainly not been lost on the field of vaccine engineering. Vaccinologists, and even some more specialized molecular engineers working on PLPs, have pursued vaccines against everything from cancer (Bryan, J. T., "Developing an HPV Vaccine to Prevent Cervical Cancer and Genital Warts," *Vaccine* 25:3001-6 (2007) and Ko et al., "Clinical Studies of Vaccines Targeting Breast Cancer," *Clinical Cancer* 9:3222-3234 (2003), which are hereby incorporated by reference in their entirety), to Alzheimer's disease, to nicotine (O'Hagan et al., "Recent Advances in the Discovery and Delivery of Vaccine Adjuvants," *Nature Reviews Drug Discovery* 2:727-35 (2003) and Singh et al., "Nanoparticles and Microparticles as Vaccine-Delivery Systems," *Expert Review of Vaccines* 6:797-808 (2007), which are hereby incorporated by reference in their entirety). While such uses of vaccines are not currently on the market (though a vaccine for leukemia therapy (Zhang et al., "A Phase-I Clinical Trial of Active Immunotherapy for Acute Leukemia Using Inactivated Autologous Leukemia Cells Mixed with IL-2, GM-CSF, and IL-6," *Leukemia Research* 29:3-9 (2005), which is hereby incorporated by reference in its entirety) could become the first FDA approved example shortly), their development speaks to a broader potential of vaccine engineering—using the immune system to alter non-pathogenic disease via relevant molecular targeting. The first target for non-pathogen vaccination is allergy. This represents an understandable middle ground: allergy is a non-pathogenic disease that the immune system is obviously highly involved with on a fundamental level, and immunomodulation therapy for the treatment of allergy is common.

Figure 19:
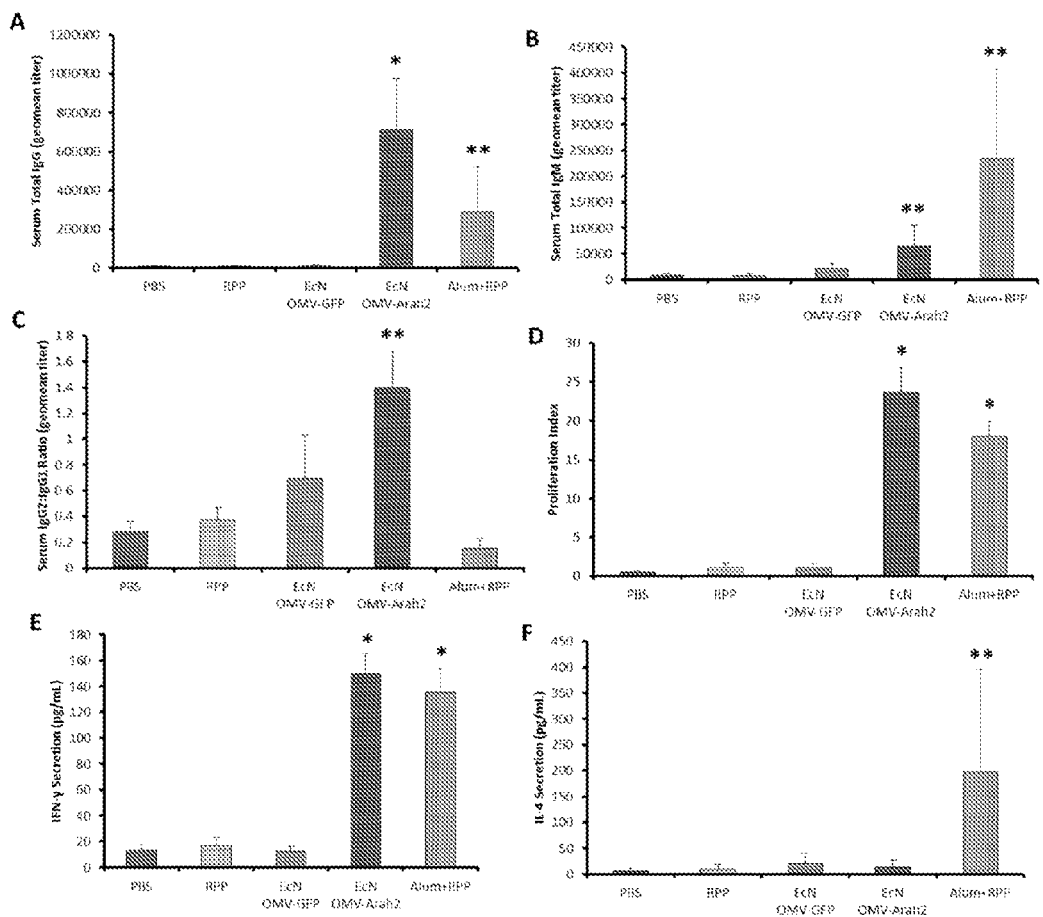
FIGS. 19A-F show EcN OMV carriers generate strong anti-Arah2 humoral and cellular immunity. Terminal data points from BALB/c mice vaccinated and boosted once with antigen-normalized (or protein normalized, as appropriate) with EcN OMVs and controls (n=5).

The model for allergy vaccination will be allergies to *Arachishypogaea*, or peanuts. 1-2% of Americans currently live with mild to severe peanut allergy, a number that has grown substantially over the past several decades at an alarming rate. Peanut exposure, even through minimal inhalation of peanut residue, can be fatal, and many school districts have outright banned peanut-containing foods as a health hazard. As a result, it represents a high-impact vaccine target (Roy et al., "Oral Gene Delivery with Chitosan—DNA Nanoparticles Generates Immunologic Protection in a Murine Model of Peanut Allergy," *Nature Medicine* 5:387-91 (1999); Pons et al., "Soy Immunotherapy for Peanut-Allergic Mice: Modulation of the Peanut-Allergic Response," *The Journal of Allergy and Clinical Immunology* 114:915-21 (2004); and Mcdermott et al., "Contribution of Ara h 2 to Peanut-Specific, Immunoglobulin E-Mediated, Cell Activation Clinical and Experimental Allergy," *Clinical and Experimental Allergy* 37:752-763 (2007), which are hereby incorporated by reference in their entirety). While most current therapy involves fairly crude methods of desensitization through variable measured antigen exposure, results are highly patient-variable and in general woefully inadequate. An EcN OMV peanut vaccine would involve a much different mechanism. Drawing on a theory first proposed by immunologists studying asthma (Bickert et al., "Probiotic *Escherichia coli* Nissle 1917 Suppresses Allergen-Induced Th2 Responses in the Airways," *International Archives of Allergy and Immunology* 149:219-30 (2009), which is hereby incorporated by reference in its entirety), it seems innate propensity to allergy can be avoided if the immune system has a strong $T_H1$-biased response to the allergen that can shut down the IgE-mediated hypersensitivity reaction characterizing most allergic attacks, especially if $T_H1$ T-cells can act in tandem with increased global IL-10 secretion following allergen exposure An assay of antigen-specific immunogenicity in BALB/c mice was performed. This was an essential first step due to the nature of the antigen subunit target, which was selected to be the peanut protein Arah2 (Mcdermott et al., "Contribution of Ara h 2 to Peanut-Specific, Immunoglobulin E-Mediated, Cell Activation Clinical and Experimental Allergy," *Clinical and Experimental Allergy* 37:752-763 (2007), which is hereby incorporated by reference in its entirety). Arah2, being a eukaryotic plant protein, posed the risk of not being sufficiently expressible in bacteria, or, if expressible, ran the risk of not folding in a fashion appropriate to generate meaningful anti-antigen specific immunity. To help ensure success, the Arah2 sequence was codon-harmonized through Invitrogen's GeneArt® Gene-Optimizer® algorithm. The resulting sequence was expressed as a ClyA-fusion and vaccinated as done previously against a positive control of alum and raw peanut protein (RPP). The immune response was then assayed as before against RPP, not purified recombinant Arah2, to ensure the desired retention of anti-antigen immunity. EcN OMV-induced humoral (FIG. 19A-19C) and cellular (FIG. 19D-19F) immunity was, as hoped, equivalent to initial observations using GFP as a model antigen, demonstrating that at least in certain cases codon harmonization is sufficient to preserve eukaryotic protein antigenicity when delivered by the EcN OMV, though further studies would be required to make conclusive statements concerning whether or not this explicitly stems from retained tertiary antigen structure. Additionally, the Arah2-specific immune response in this study is clearly sufficient to warrant a more meaningful trial in a murine hypersensitivity model.

Discussion of Examples 1-6

While being an interest of the immunological community for decades, probiotic bacteria remain something of an enigma when it comes to medical applications. Utility of their potent immunomodulatory capacity has been reserved primarily for nutritional supplement-based approaches to managing clinical conditions such as irritable bowel disease and general allergy (Trebichaysky et al., "Modulation of Natural Immunity in the Gut by *Escherichia coli* Strain Nissle 1917," *Nutr. Rev.* 68:459-464 (2010), which is hereby incorporated by reference in its entirety). Research into their mechanism of action has been on the rise in recent years, however, and the emerging picture concerning their capacity for locally (Sturm et al., "*Escherichia coli* Nissle 1917 Distinctively Modulates T-Cell Cycling and Expansion via Toll-Like Receptor 2 Signaling," *Infect. Immunol.* 73:1452-1465 (2005) and Guzy et al., "The Probiotic *Escherichia coli* Strain Nissle 1917 Induces Gammadelta T Cell Apoptosis via Caspase- and FasL-Dependent Pathways," *Int. Immun.* 20:829-840 (2008), which are hereby incorporated by reference in their entirety) and globally (Trebichaysky et al., "Modulation of Natural Immunity in the Gut by *Escherichia coli* Strain Nissle 1917," *Nutr. Rev.* 68:459-464 (2010), which is hereby incorporated by reference in its entirety) altering the body's immunity indicates the ability to strike a non-trivial balance between actively targeting and antagonizing key immune cells while simultaneously suppressing components that would exacerbate an active response. Such complexity is often the hallmark of organisms that have evolved to have an intricate and potent interaction with the host immune system, and it is this complexity that has made probiotic bacteria simultaneously attractive to study but difficult to apply in the medical field.

In this study, the efficacy of the OMV production process of isolating the PAMP-driven immunostimulatory nature of probiotic bacteria for recombinant subunit vaccine delivery applications was assessed. OMVs are bacterially-derived, nanoscale proteoliposomes naturally enriched with immunoactive components ranging from LPS and BLPs to lumen-sequestered "vita-PAMPS", creating intriguing pathogen-like particles—that is, particles the immune system can be tricked into believing are, for all practical intents and purposes, active and dangerous pathogens. OMVs have the unique ability to combine the biomolecular advantages of using a specific pathogen as a delivery vector with the intrinsic advantages of nanoscale delivery such as enhanced cellular uptake via ligand-dependent surface receptor cross-linking (Mann et al., "Lipid Vesicle Size of an Oral Influence Vaccine Delivery Vehicle Influences the Th1/Th2 Bias in the Immune Response and Protection Against Infection," *Vaccine* 27:3643-3649 (2009), which is hereby incorporated by reference in its entirety). By using a fusion-chimera approach to exogenous antigen production incorporating membrane-targeting ClyA, a vaccine carrier particle with surface displayed antigen that could be produced as a single-component, self-adjuvanting entity in simple bacterial culture production that can take full advantage of the attractive vaccine carrier features of the bacterial OMV was able to be created.

Collectively, the findings indicate that these EcN OMVs generate a relatively rare adaptive response to a recombinant antigen that current adjuvant technology fails to consistently and/or simplistically achieve: a functional anti-antigen humoral response more than 100-fold stronger than the antigen alone is capable of, indicative of a response strong enough to confer immunity (Weeratna et al., "CpG DNA Induces Stronger Immune Responses with Less Toxicity than Other Adjuvants," *Vaccine* 18:1755-1762 (2000), which is hereby incorporated by reference in its entirety), coupled with a T-cell response whose strength and $T_H1$ specificity suggest the conferral of cellular immunity on a level that would substantially enhance efficacy against intracellular pathogens (Mosmann et al., "TH1 and TH2 Cells: Different Patterns of Lymphokine Secretion Lead to Different Functional Properties," *Annu. Rev. Immunol.* 7:145-173 (1989), which is hereby incorporated by reference in its entirety). This allows the EcN OMV vaccine carrier described here to fill an important niche in vaccine engineering and therefore address the crucial unmet clinical need of a practical and widely applicable platform for creating vaccines against a variety of high-profile intracellular pathogens. Moreover, probing the way these OMVs directly interface on a cellular level with both innate and adaptive immunity reveals a unique capacity for robust and multi-faceted stimulation that is dependent not merely on the nature of bacterial OMVs in general, but specifically reflects the platform's ability to harness a specific advantage of the EcN bacteria. While stopping short of being able to fully characterize the exact molecular pathways isolated from the EcN outer membrane, the findings represent the first successful attempt at harnessing the immunostimulatory capacity of a probiotic bacterial strain for recombinant subunit vaccine applications. By isolating the targeted adjuvant component of a highly immunoactive, yet thoroughly immunosuppressive bacterial strain, an antigen delivery system capable of robust and complete innate and adaptive immune stimulation was generated.

In engineering and optimizing the use of a bacterial OMV as a vaccine delivery carrier, there was a specific interest in demonstrating how the field's defining transition from using whole pathogens to focusing on isolated antigens need not sacrifice the myriad advantages of holistic pathogen-host responses. OMVs as exogenous antigen carriers have been previously established (Chen et al., "Delivery of Foreign Antigens by Engineered Outer Membrane Vesicle Vaccines," *Proc. Nat. Acad. Sci. USA* 107:3099-3104 (2010) and Muralinath et al., "Immunization with *Salmonella Enterica* Serovar *Typhimurium*-Derived Outer Membrane Vesicles Delivering the Pneumococcal Protein PspA Confers Protection Against Challenge with *Streptococcus pneumonia*," *Infect. Immun.* 79:887-894 (2011), which are hereby incorporated by reference in their entirety) to be a promising vaccine technology. The goal in this study, therefore, was to establish the capacity of rationally engineered OMV-based carriers to bridge the gap between some of the more complex advantages still retained exclusively by whole-pathogen vaccine approaches and the more universally applicable platform of biomolecular nanocarriers. The capacity of engineered OMVs to isolate unique, strain-dependent self-adjuvancy and targeting that biases immunity strongly towards a $T_H1$ response is the core discovery of this study, but it is only one of several advantages illuminated. For example, the vaccine carrier's observed induction of robust humoral, $T_H1$-indicative immunity is particularly meaningful when considering the model antigen was additionally presented to the immune system as a functionally folded "surface antigen" on the adjuvanting OMV particle. Unlike many recently developed alternative adjuvant systems designed to enhance $T_H1$-type immunity induction (Schijns et al., "Vaccine Immunopotentiators of the Future," *Clin. Pharmacol. Ther.* 82:750-755 (2007) and Sanders et al., "ISCOM-Based Vaccines: The Second Decade," *Immunol Cell Biol.* 83:119-128 (2005), which are hereby incorporated by reference in their entirety), the EcN-derived OMVs have a greater capacity to generate recognition immunity against a full range of linear epitopes (via MHC-facilitated T-cell receptor presentation) as well as conformational epitopes (via direct surface presentation to B-cell receptors). In the past, the field had been forced to primarily write such an advantage off as a necessary loss to move beyond working with whole pathogens. As the platform is specifically derived from the very biomolecular material responsible for natural and diverse antigen presentation by bacteria, this advantage is preserved and was demonstrated to likely enhance influenza HA cross-protection beyond traditional gold standard adjuvants.

Moreover, this approach to vaccine carrier engineering does not merely preserve advantages of working with whole pathogens—it additionally provides avenues for rational tuning and optimization of antigen presentation as well as the targeted immune response itself. By demonstrating platform applicability to both a traditional bacterially-expressed exogenous protein, GFP, as well as an immunologically important viral antigen, influenza HA, it has been demonstrated that simple protein engineering techniques can lead to the successful coupling of a bacterially stimulated immune response and a non-bacterial pathogen. Additionally, the findings concerning LPS endotoxicity mutation indicates a capacity through biomolecular engineering to tune dependence on endotoxicity to a minimal level that reduces the vaccine's side effects without sacrificing the innate immunostimulatory advantage of probiotic strain-derived OMVs, giving the platform an impactful advantage over other bacterially-derived technologies. Additional avenues of rational, multivalent modification—such as polyvalent antigen cocktail inclusion (Fischer et al., "Polyvalent Vaccines for Optimal Coverage of Potential T-Cell Epitopes in Global HIV-1 Variants," *Nat. Med.* 13:100-106 (2007), which is hereby incorporated by reference in its entirety), pathogen-targeted glycosylation (Valderrama-Rincon et al., "An Engineered Eukaryotic Protein Glycosylation Pathway in *Escherichia coli,*" *Nat. Chem. Biol.* 8:434-436 (2012), which is hereby incorporated by reference in its entirety), and even particle size modification (Mann et al., "Lipid Vesicle Size of an Oral Influence Vaccine Delivery Vehicle Influences the Th1/Th2 Bias in the Immune Response and Protection Against Infection," Vaccine 27:3643-3649 (2009), which is hereby incorporated by reference in its entirety) through additional genetic deregulation of vesiculation control—further contribute to the diverse potential of this platform to facilitate vaccine engineering's transition from making simple stimulatory particles to utilizing more advanced and holistic molecular mimicry of pathogen identity.

The study presented here builds a case for the efficacy of a bacterially-derived, pathogen-like particle vaccine delivery carrier for a broad range of vaccine applications. By harnessing the potent and broadly integrated immunostimulation of probiotic bacteria and seamlessly merging it with the widely-used capacity of bacteria to recombinantly express exogenous antigens from almost every classification of vaccine target, a platform that merely requires the substitution of an antigenic gene of interest for the generation of far-reaching clinical impact has been created. In this way, it is anticipated that the unique combination of non-infectious immunomodulation and a capacity for diverse, rational molecular engineering—without sacrificing simple and scalable production capabilities—can provide a template for the development of potent new vaccines derived from previously overlooked biological sources.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A probiotic-derived vesicle displaying a fusion protein, wherein said fusion protein comprises at least a portion of a transport protein coupled to at least a portion of one or more antigenic proteins or peptides.

2. The probiotic-derived vesicle of claim 1, wherein the transport protein is an adhesin, immunomodulatory compound, protease, or toxin.

3. The probiotic-derived vesicle of claim 2, wherein the transport protein is ClyA.

4. The probiotic-derived vesicle cell of claim 1, wherein the antigenic protein or peptide is derived from pathogenic bacterial, fungal or viral organisms, *Streptococcus* species, *Candida* species, *Brucella* species, *Salmonella* species, *Shigella* species, *Pseudomonas* species, *Bordetella* species, *Clostridium* species, Norwalk virus, *Bacillus anthracis*, *Mycobacterium tuberculosis*, human immunodeficiency virus (HIV), *Chlamydia* species, Human Papillomaviruses, Influenza virus, Paramyxovirus species, Herpes virus, Cytomegalovirus, Varicella-Zoster virus, Epstein-Barr virus, Hepatitis viruses, *Plasmodium* species, *Trichomonas* species, sexually transmitted disease agents, viral encephalitis agents, protozoan disease agents, fungal disease agents, bacterial disease agents, cancer cells, or combinations.

5. The probiotic-derived vesicle of claim 1, wherein the probiotic-derived vesicle is from a cell selected from the group consisting of *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus reuteri, Lactobacillus rhamnosus, Lactobacillus johnsonii, Lactobacillus plantarum, Lactobacillus fermentum, Lactococcus lactis, Streptococcus thermophilus, Lactococcus lactis, Lactococcus diacetylactis, Lactococcus cremoris, Lactobacillus bulgaricus, Lactobacillus helveticus, Lactobacillus delbrueckii, Escherichia coli*, and mixtures thereof.

6. The probiotic-derived vesicle of claim 5, wherein the probiotic-derived vesicle is from *Escherichia coli* Nissle.

7. The probiotic-derived vesicle of claim 6, wherein the vesicle displays a fusion protein comprising at least a portion of a ClyA protein coupled to at least a portion of one or more antigenic proteins or peptides.

8. A probiotic-derived vesicle displaying a fusion protein, wherein said fusion protein comprises at least a portion of a transport protein coupled to at least a portion of one or more antigenic food allergy proteins or peptides.

9. The probiotic-derived vesicle of claim 8, wherein the transport protein is an adhesin, immunomodulatory compound, protease, or toxin.

10. The probiotic-derived vesicle of claim 8, wherein the transport protein is ClyA.

11. The probiotic-derived vesicle of claim 8, wherein the antigenic food allergy proteins or peptides are derived from milk, eggs, fish, crustacean shellfish, tree nuts, peanuts, wheat, coconut, and soybeans.

12. The probiotic-derived vesicle of claim 11, wherein the food allergy is against peanuts and the antigenic food allergy protein or peptide is Arha2.

13. The probiotic-derived vesicle of claim 8, wherein the probiotic-derived vesicle is from a cell selected from the group consisting of *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus reuteri, Lactobacillus rhamnosus, Lactobacillus johnsonii, Lactobacillus plantarum, Lactobacillus fermentum, Lactococcus lactis, Streptococcus thermophilus, Lactococcus lactis, Lactococcus diacetylactis, Lactococcus cremoris, Lactobacillus bulgaricus, Lactobacillus helveticus, Lactobacillus delbrueckii, Escherichia coli*, and mixtures thereof.

14. The probiotic-derived vesicle of claim 13, wherein the probiotic-derived vesicle is from *Escherichia coli* Nissle.

15. A probiotic-derived vesicle displaying a fusion protein, wherein said fusion protein comprises at least a portion of a transport protein coupled to at least a portion of one or more antigenic viral proteins or peptides.

16. The probiotic-derived vesicle of claim 15, wherein the transport protein is an adhesin, immunomodulatory compound, protease, or toxin.

17. The probiotic-derived vesicle of claim 15, wherein the transport protein is ClyA.

18. The probiotic-derived vesicle of claim 15, wherein the antigenic viral protein or peptide is from Human Immunodeficiency Virus (HIV), influenza A virus, influenza B virus, influenza C virus, rabies virus, vesicular stomatitis virus, respiratory syncytial virus, measles virus, parainfluenza virus, mumps virus, yellow fever virus, west nile virus, dengue virus, rubella virus, sindbis virus, semliki forest virus, ross river virus, rotavirus, parvovirus, JC polyoma virus, BK polyoma virus, Human papillomavirus (HPV), adenovirus, hepatitis B virus, hepatitis C virus, hepatitis A virus, hepatitis E virus, Human herpesvirus, vaccinia virus, monkeypox virus, cowpox virus, human T-cell leukemia virus, coxsackie virus, polio virus, rhinovirus, enterovirus, echovirus, ebola virus, coronavirus, variola virus, hantaan virus, adeno-associated virus, astrovirus, hendra virus, lassa virus, nipah virus, Marburg virus, and Norwalk virus.

19. The probiotic-derived vesicle of claim 18, wherein the virus is influenza and the antigenic viral protein or peptide is H1N1 hemagglutinin.

20. The probiotic-derived vesicle of claim 15, wherein the probiotic-derived vesicle is from a cell selected from the group consisting of *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus reuteri, Lactobacillus rhamnosus, Lactobacillus johnsonii, Lactobacillus plantarum, Lactobacillus fermentum, Lactococcus lactis, Streptococcus thermophilus, Lactococcus lactis, Lactococcus diacetylactis, Lactococcus cremoris, Lactobacillus bulgaricus, Lactobacillus helveticus, Lactobacillus delbrueckii, Escherichia coli*, and mixtures thereof.

21. The probiotic-derived vesicle of claim 20, wherein the probiotic-derived vesicle is from *Escherichia coli* Nissle.

22. A probiotic-derived vesicle displaying a fusion protein, wherein said fusion protein comprises at least a portion of a transport protein coupled to at least a portion of one or more antigenic intracellular bacterial proteins or peptides.

23. The probiotic-derived vesicle of claim 22, wherein the transport protein is an adhesin, immunomodulatory compound, protease, or toxin.

24. The probiotic-derived vesicle of claim 22, wherein the transport protein is ClyA.

25. The probiotic-derived vesicle of claim 22, wherein the antigenic intracellular bacterial protein or peptide is from *Chlamydophila, Ehrlichia, Rickettsia, Mycobacterium, Brucella, Francisella, Legionella*, or *Listeria*.

26. The probiotic-derived vesicle of claim 25, wherein the bacteria is from *Mycobacterium* paratuberculosis and the antigenic intracellular bacterial protein is 74F protein.

27. The probiotic-derived vesicle of claim 22, wherein the probiotic-derived vesicle is from a cell selected from the group consisting of *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus reuteri, Lactobacillus rhamnosus, Lactobacillus johnsonii, Lactobacillus plantarum, Lactobacillus fermentum, Lactococcus lactis, Streptococcus thermophilus, Lactococcus lactis, Lactococcus diacetylactis, Lactococcus cremoris, Lactobacillus bulgaricus, Lactobacillus helveticus, Lactobacillus delbrueckii, Escherichia coli*, and mixtures thereof.

28. The probiotic-derived vesicle of claim 27, wherein the probiotic-derived vesicle is from *Escherichia coli* Nissle.

29. A method of eliciting an immune response in a mammal, said method comprising:
providing the probiotic-derived vesicle of claim 1 and
administering the probiotic-derived vesicle to the mammal under conditions effective to elicit the immune response.

30. The method according to claim 29, wherein the transport protein is an adhesin, immunomodulatory compound, protease, or toxin.

31. The method according to claim 29, wherein the transport protein is ClyA.

32. The method according to claim 29, wherein the antigenic protein or peptide is derived from pathogenic bacterial, fungal or viral organisms, *Streptococcus* species, *Candida* species, *Brucella* species, *Salmonella* species, *Shigella* species, *Pseudomonas* species, *Bordetella* species, *Clostridium* species, Norwalk virus, *Bacillus anthracis, Mycobacterium tuberculosis*, human immunodeficiency virus (HIV), *Chlamydia* species, Human Papillomaviruses, Influenza virus, Paramyxovirus species, Herpes virus, Cytomegalovirus, Varicella-Zoster virus, Epstein-Barr virus, Hepatitis viruses, *Plasmodium* species, *Trichomonas* species, sexually transmitted disease agents, viral encephalitis agents, protozoan disease agents, fungal disease agents, bacterial disease agents, cancer cells, or combinations.

33. The method according to claim 29, wherein the probiotic-derived vesicle is from a cell selected from the group consisting of *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus reuteri, Lactobacillus rhamnosus, Lactobacillus johnsonii, Lactobacillus plantarum, Lactobacillus fermentum, Lactococcus lactis, Streptococcus thermophilus, Lactococcus lactis, Lactococcus diacetylactis, Lactococcus cremoris, Lactobacillus bulgaricus, Lactobacillus helveticus, Lactobacillus delbrueckii, Escherichia coli*, and mixtures thereof.

34. The method according to claim 31, wherein the probiotic-derived vesicle is from *Escherichia coli* Nissle.

35. A method of immunizing a subject against a food allergy, said method comprising:
selecting a subject having a food allergy;
providing the probiotic-derived vesicle of claim 8; and
administering the probiotic-derived vesicle to the selected subject under conditions effective to immunize the subject against the food allergy.

36. The method according to claim 35, wherein the food allergy is against milk, eggs, fish, crustacean shellfish, tree nuts, peanuts, wheat, coconut, and soybeans.

37. The method according to claim 36, wherein the food allergy is against peanuts and the antigenic protein or peptide is Arah2.

38. A method of immunizing a subject against a viral infection, said method comprising:
selecting a subject at risk of developing a viral infection;
providing the probiotic-derived vesicle of claim 15; and
administering the probiotic cell to the selected subject under conditions effective to immunize the subject against the viral infection.

39. The method according to claim 38, wherein the antigenic viral protein or peptide is from Human Immunodeficiency Virus (HIV), influenza A virus, influenza B virus, influenza C virus, rabies virus, vesicular stomatitis virus, respiratory syncytial virus, measles virus, parainfluenza virus, mumps virus, yellow fever virus, west nile virus, dengue virus, rubella virus, sindbis virus, semliki forest virus, ross river virus, rotavirus, parvovirus, JC polyoma virus, BK polyoma virus, Human papillomavirus (HPV), adenovirus, hepatitis B virus, hepatitis C virus, hepatitis A virus, hepatitis E virus, Human herpesvirus, vaccinia virus, monkeypox virus, cowpox virus, human T-cell leukemia virus, coxsackie virus, polio virus, rhinovirus, enterovirus, echovirus, ebola virus, coronavirus, variola virus, hantaan virus, adeno-associated virus, astrovirus, hendra virus, lassa virus, nipah virus, Marburg virus, and Norwalk virus.

40. The method according to claim 39, wherein the viral infection is influenza and the antigenic protein or peptide is H1N1 hemagglutinin.

41. A method of immunizing an animal against an intracellular bacterial infection, said method comprising:
selecting an animal at risk of developing an intracellular bacterial infection;

providing the probiotic-derived vesicle of claim 22; and administering the probiotic-derived vesicle to the selected animal under conditions effective to immunize the animal against the intracellular bacterial infection.

42. The method according to claim 41, wherein the animal is a ruminant.

43. The method according to claim 41, wherein the intracellular bacteria is *Chlamydophila, Ehrlichia, Rickettsia, Mycobacterium, Brucella, Francisella, Legionella*, or *Listeria*.

44. The method according to claim 43, wherein the intracellular bacteria is *Mycobacterium paratuberculosis* and the antigenic protein or peptide is *Mycobacterium paratuberculosis* 74F protein.

\* \* \* \* \*